(12) United States Patent
Evans

(10) Patent No.: US 7,824,414 B2
(45) Date of Patent: Nov. 2, 2010

(54) SYSTEM AND DEVICES FOR THE REPAIR OF A VERTEBRAL DISC DEFECT

(75) Inventor: Douglas G. Evans, Downingtown, PA (US)

(73) Assignee: Kensey Nash Corporation, Exton, PA (US)

( * ) Notice: Subject to any disclaimer, the term of this patent is extended or adjusted under 35 U.S.C. 154(b) by 894 days.

(21) Appl. No.: 11/187,064

(22) Filed: Jul. 22, 2005

(65) Prior Publication Data

US 2007/0043374 A1    Feb. 22, 2007

(51) Int. Cl.
A61F 2/00 (2006.01)
(52) U.S. Cl. .......................................... 606/99; 606/151
(58) Field of Classification Search ................ 606/151, 606/139, 144, 145, 142, 99
See application file for complete search history.

(56) References Cited

U.S. PATENT DOCUMENTS

| | | | |
|---|---|---|---|
| 4,235,238 A | 11/1980 | Ogiu et al. | |
| 4,472,840 A | 9/1984 | Jefferies | |
| 4,563,489 A | 1/1986 | Urist | |
| 4,669,473 A | 6/1987 | Richards et al. | |
| 4,678,470 A | 7/1987 | Nashef et al. | |
| 4,741,330 A | 5/1988 | Hayhurst | |
| 4,750,492 A | 6/1988 | Jacobs | |
| 5,021,059 A | 6/1991 | Kensey et al. | |
| 5,041,129 A | 8/1991 | Hayhurst et al. | |
| 5,269,809 A | 12/1993 | Hayhurst et al. | |
| 5,545,178 A * | 8/1996 | Kensey et al. | ............... 606/213 |
| 6,136,010 A | 10/2000 | Modesitt et al. | |
| 6,180,605 B1 | 1/2001 | Chen et al. | |
| 6,180,606 B1 | 1/2001 | Chen et al. | |
| 6,224,630 B1 | 5/2001 | Bao et al. | |
| 6,245,079 B1 * | 6/2001 | Nobles et al. | ............... 606/144 |
| 6,245,107 B1 | 6/2001 | Ferree | |
| 6,371,990 B1 | 4/2002 | Ferree | |
| 6,402,750 B1 | 6/2002 | Atkinson et al. | |
| 6,425,900 B1 * | 7/2002 | Knodel et al. | ............... 606/139 |
| 6,428,576 B1 * | 8/2002 | Haldimann | ............... 623/17.16 |
| 6,508,839 B1 | 1/2003 | Lambrecht et al. | |
| 6,530,933 B1 | 3/2003 | Yeung et al. | |
| 6,579,291 B1 | 6/2003 | Keith et al. | |
| 6,592,625 B2 | 7/2003 | Cauthen | |
| 6,626,916 B1 | 9/2003 | Yeung et al. | |
| 6,805,695 B2 | 10/2004 | Keith et al. | |
| 6,835,205 B2 | 12/2004 | Atkinson et al. | |
| 6,911,034 B2 * | 6/2005 | Nobles et al. | ............... 606/144 |

(Continued)

FOREIGN PATENT DOCUMENTS

WO    WO 01/95818 A1    12/2001

(Continued)

*Primary Examiner*—Eduardo C Robert
*Assistant Examiner*—Elena B Fisher
(74) *Attorney, Agent, or Firm*—Jeffrey R. Ramberg

(57) ABSTRACT

A system for repairing a vertebral disc defect, such as hernia or bulge, a full or partial tear in the annulus, or a weakened annulus wall as a result of an excision procedure. The system introduces a treatment device arranged to repair the defect, and may prevent the leakage of fluid from the nucleus. The components of the device may be resorbable materials, and may induce the ingrowth of cellular material into the components. The system may feature a locating device to ensure proper placement of the treatment device.

8 Claims, 11 Drawing Sheets

U.S. PATENT DOCUMENTS

| | | |
|---|---|---|
| 2002/0049453 A1* | 4/2002 | Nobles et al. ............... 606/139 |
| 2002/0151980 A1 | 10/2002 | Cauthen |
| 2003/0074075 A1 | 4/2003 | Thomas et al. |
| 2003/0195514 A1* | 10/2003 | Trieu et al. .................... 606/61 |
| 2003/0220693 A1 | 11/2003 | Cauthen, III |
| 2004/0097980 A1 | 5/2004 | Ferree |
| 2005/0256532 A1* | 11/2005 | Nayak et al. ................ 606/151 |
| 2006/0253152 A1 | 11/2006 | Evans et al. |

FOREIGN PATENT DOCUMENTS

| | | |
|---|---|---|
| WO | WO 2005/020859 A1 | 3/2005 |

* cited by examiner

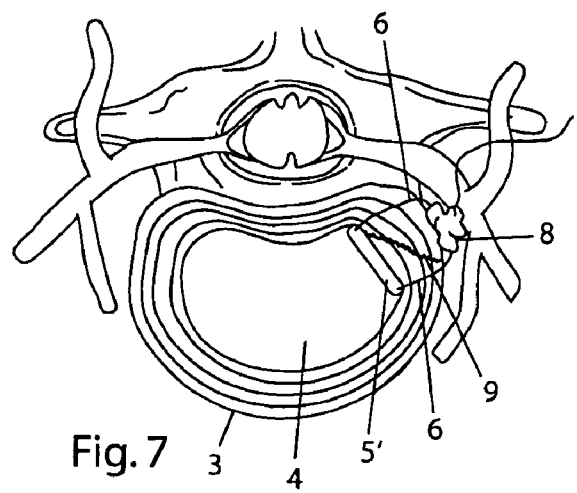
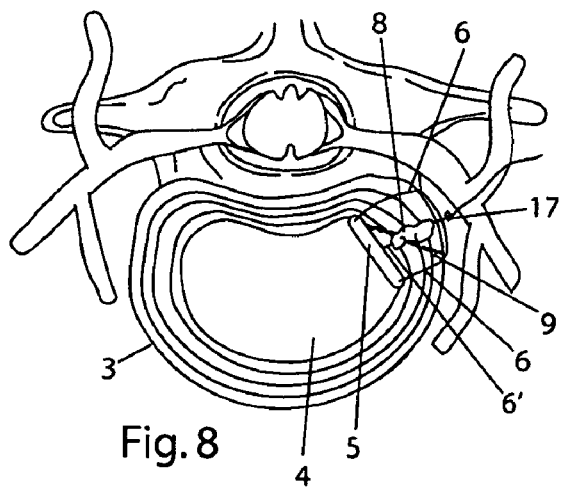
Fig. 7            Fig. 8
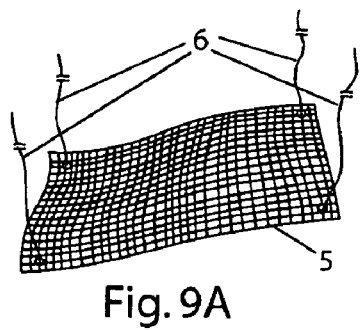
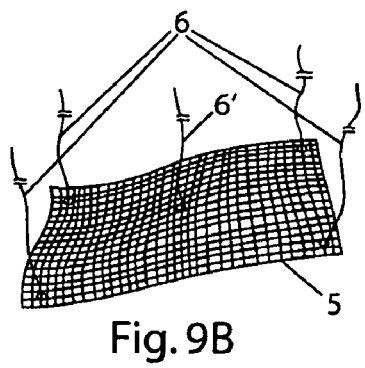
Fig. 9A            Fig. 9B
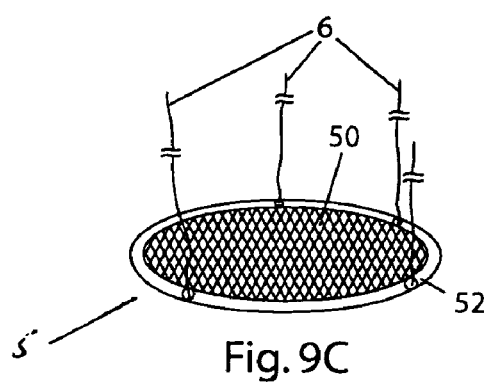
Fig. 9C

SYSTEM AND DEVICES FOR THE REPAIR OF A VERTEBRAL DISC DEFECT

FIELD OF THE INVENTION

The invention relates generally to methods and devices for human surgery, and in particular these methods and devices may be useful for spinal surgery. More particularly, certain embodiments of the invention relate to devices and methods for treating injuries, defects or surgical procedures associated with the intervertebral disc.

BACKGROUND OF THE INVENTION

Injuries to the human spine and subsequent pain are one of the most prevalent debilitating conditions affecting the human population. For many of those affected, no position can ease the pain or discomfort associated with spinal injuries or deformities. Such spine related pain can lead to decreased productivity due to loss of work hours, addiction to pain-killing drugs, emotional distress, and prolonged hospital stays. The economic impact of such problems is significant. One common cause for many instances of chronic pain is the bulging, or herniation of the intervertebral disc.

The intervertebral disc is made of two parts, a tough collagen outer layer, known as the annulus fibrosus (hereinafter also referred to as "AF" or "annulus"), and a soft central core known as the nucleus pulposus (hereinafter also referred to as "NP" or "nucleus"). The annulus is composed of numerous concentric rings or layers of fibrocartilaginous tissue. Fibers in each ring cross diagonally, and the rings attach to each other with additional radial fibers. The rings are thicker anteriorly (ventrally) than posteriorly (dorsally). The nucleus is a gelatinous material, which forms the center of the disc. The discs tend to vary in size and shape with their position in the spine. The nucleus is composed of a loose, nonoriented, collagen fibril framework supporting a network of cells resembling fibrocytes and chondrocytes. This entire structure is embedded in a gelatinous matrix of various glucosaminoglycans, water, and salts. This material is usually under considerable pressure and is restrained by the annulus.

A tear or weakening in the layers of the annulus fibrosus portion of the disc can allow the soft center portion of the disc (the nucleus) to leak out of the annulus, alternatively, the weakened annulus may simply bulge. A ruptured disc may allow the leaking nucleus pulposus material to press up against a spinal nerve root or spinal cord, causing pain, numbness, tingling and/or weakness in a person's extremities. Herniated discs may occur at any level of the spine, but are more common in the lumbar area, followed in frequency of occurrence by the thoracic region and cervical region. Weakening or tearing of the annulus fibrosus may also result in bulging of the annulus fibrosus due to pressure of the nucleus pulposus against the annulus. The bulging tissue may also impinge upon the nerve root or spinal column, causing pain.

The traditional surgical method for treating a damaged, bulging, or herniated disc involves tissue removing procedures to relieve the impingement of the annulus fibrosus or the nucleus pulposus from the surrounding nerves. The procedure is commonly known as a discectomy, and consists of the removal of at least a portion of the disc; it may be performed in an open procedure, a minimally invasive procedure, or an endoscopically assisted procedure. These procedures generally result in a large defect of the annulus fibrosus and in a certain percentage of cases, may lead to progressive degradation of the disc, both nucleus pulposus and annulus fibrosus, listhesis of adjacent vertebral bodies, stenosis of the nerve canals and increases in related pain symptoms. A means of mechanically and/or biologically repairing the annulus fibrosus may delay or prevent this degeneration cascade of the disc.

Newer technologies and procedures, such as nucleus replacement with injectable or solid prosthetic nucleus devices may also result in a breach in the otherwise coherent annulus fibrosis. In these cases, it is desirable to mechanically close, or otherwise repair the defect in the annulus created to insert the prosthetic material and prevent such material from leakage and extravasation.

The annulus fibrosis (AF) of the intervertebral spinal disc is a lamellar configuration of collagen layers intended to maintain the soft viscous internal nucleus pulposus (NP), provide for motion and linkage of the adjacent vertebral bodies (VB). Certain degenerative or pathologic changes may occur either within the NP which can lead to over stress of the AF and subsequent damage to or tearing of the AF. If left untreated, herniation of the NP may occur, most importantly, the herniation may progress posteriorly toward the spinal cord and major nerve roots. The most common resulting symptoms are pain radiating along a compressed nerve and low back pain, both of which can be crippling for the patient. The AF may also be torn through traumatic injury, which can lead to progressive degenerative changes and herniation or ultimately listhesis of the adjacent VB, degenerative changes in the lumbar spine that may result in a loss of spinal stability and subluxation of one vertebra relative to another.

Herniation may be caused by, or be the result of weakening in the AF. Secondary to physiologic changes of the AF or NP, the AF may weaken and protrude from its normal anatomic space, similar to an air bubble bulge in a car tire, or in more severe cases, the AF may tear and allow extravasation of the NP contents to the surrounding anatomy. Symptoms may arise when the herniation or leakage of the NP impinges on the nerve root or spinal cord. There are therapies currently utilized for treatment of the herniation of a vertebral disc, and the resultant pain, starting with conservative therapies such as bed rest and pain medicines, to more invasive therapies, such as epidural injections, open or minimally invasive discectomies or aggressive therapies, such as complete discectomy and fusion of the disc space and adjacent vertebrae.

The prior art describes various procedures and devices for repairing damage to the vertebral disc. The prior art describes repairing a herniated disk by various means, including prosthetic implants, and stressed members. For example, in U.S. Pat. No. 6,805,695, Keith et al. disclose devices and methods of reinforcing an annulus of the disc by introducing a circumferential reinforcement member around the annulus of the disc, or through the annulus and nucleus of the disc.

In U.S. Pat. No. 6,371,990, Ferree discloses an apparatus and method for repairing annular tears and the prevention of further annular tears. Ferree seeks to control vertebral motion by augmenting the annulus with an implant, thereby minimizing the opportunity for annular tears. The augmenting implant is described as being a mesh that may be stapled into the interior of the annulus.

Ferree also discloses in U.S. Patent Application 2004/0097980 an expandable material to fill a defect in a disk, and that the material may be anchored to the annulus with respect to the void filled. In an embodiment, the anchors are described as penetrating through the outer wall of the disc and serve to hold the flexible implant material in place.

Yeung discloses in U.S. Pat. No. 6,530,933 a method and apparatus for herniated disc repair using resilient fastener elements that are implanted and spring back to an original shape to apply tension through gripping elements to hold tightly to the annulus. In an alternative embodiment, the annulus repair technique utilizes a suture affixed to a dumbbell shaped rod to serve as an anchor. The anchor is placed against the outside surface of the annulus, and the suture extends across the interior of the vertebral disc through the nucleus pulposus and out the other side of the disk, such that tension may placed against the disc to repair the hernia, and the tension may be maintained through the use of a washer and suture locking element, such as a knot. With this alternative embodiment, a sealing material may optionally be placed underneath the washer.

In U.S. Pat. No. 6,592,625, Cauthen describes annular repair or reconstruction by insertion of a collapsible patch into the subannular space, whereupon the patch expands to fill the gap and seal off the opening from the escape of nucleus material. Cauthen describes his device as being useful to restore integrity after damage or discectomy to alleviate a herniated vertebral disc; Cauthen does not obviate the need for the discectomy procedure to repair a herniated disc.

In U.S. Pat. No. 6,224,630, Bao describes the repair of an intervertebral disc using an expandable porous material that is inserted into an aperture, and subsequently becomes more permanently secured as the ingrowth of tissue into the pores is actively facilitated. Bao creates a device having a tamponade effect where the swelling of the material provides securement and does not describe a more secure mechanical anchorage using a rigid component in combination with a tissue regenerative material.

The prior art also describes various methods for sealing a percutaneous closure, for example, Kensey et al. in U.S. Pat. No. 5,545,178 describe a system for sealing a puncture made through skin and having a tract extending through to underlying tissue. The puncture closure system consists of an anchor introduced into the underlying tissue and having a filament attached thereto, the filament extends out from the puncture, and facilitates the introduction of a plug material into the tract, whereupon tension is maintained through the use of a holding member. Kensey et al. does not describe the sealing of multiple sites through the employment of a single device, nor is the employment of multiple anchors or plugs on a single filament described.

In U.S. Pat. No. 6,136,010, Modesitt et al. describe a system for suturing vascular puncture sites located at the distal end of a percutaneous tissue tract. The system consists of a suture introduced into the tissue surrounding the puncture. Said system is not suitable for closing defects in the annulus as it relies on the ability to re-approximate tissues around a defect in order to close the opening and prevent tissue from exiting through the puncture.

In U.S. Pat. No. 5,728,114, Evans et al. describe an apparatus for reducing bleeding from a percutaneous arterial puncture. The apparatus comprises a mass of material for inhibiting blood flow, a suture, and means for holding the material at the desired site. For reasons that will become apparent later, said system is not optimal for closing defects in the annulus as it is better suited to deliver a material to the outside of a tissue defect.

The prior art does not describe a device wherein the device may be capable of being implanted arthroscopically, among other methods known in the art, and is arranged to prevent the escape of nucleus pulposus from a defect in the annulus, while providing support to the defect, securement, and effective sealing means in a single device.

Accordingly, there is a need for a system or device that is capable of meeting these and other objectives, wherein the system provides means for minimally invasive delivery of a device that provides tissue support, incorporates a barrier element to assist with defect closure, a secure sealing means for positioning at the defect, securement means for holding the device in place, as well as the ability to provide for cellular infiltration and subsequent repair occurring in or around the annulus fibrosis. Furthermore, there is a need for a device capable of preserving or restoring normal annulus geometry (e.g., repairing a herniated disc), wherein there is support and secured sealing provided at each point of penetration or defect in the annulus.

It is the intent of the present invention to overcome these and other shortcomings of the prior art.

SUMMARY OF THE INVENTION

Various embodiments of the current invention strive to overcome these various shortcomings in the prior art. These embodiments allow for singular devices, or combinations of barriers, anchors or fastening devices which prevent the escape of nucleus material or nucleus replacement and/or other therapeutic materials while providing support to the annulus, sealing elements, securement elements, as well as components for restoring or maintaining satisfactory disc geometry and providing the scaffold for regeneration of the damaged annulus and other tissues.

Certain of these embodiments have barriers and or anchors (e.g. membranes, plates, fabrics, meshes, anchors, etc.), which may be deployed in a manner associated with one or both sides of the annulus wall. The barrier member, or barrier means, serves to bridge any gap between the opposing edges of the opening or defect. Once the barrier is secured adjacent to the defect, it serves to prevent tissues, such as nucleus material, from migrating through the defect. The barrier may also be suitable for helping to contain nucleus replacement materials within the nucleus portion of the annulus. In some instances, the opening in the annulus will be such that the edges of the defect can be drawn together with the filament portion of this invention. In this instance, the barrier provides reinforcement or support to the tissue at the defect site. In some embodiments, securement of the barrier to the defect site will thereby create and exert pressure on the annulus wall. This pressure alone may serve to support and/or seal the annulus. In some embodiments, combinations of barriers are used at multiple locations with respect to the annulus. The barriers themselves may feature or further be utilized in combination with a sealing means (e.g., elastic biomaterials, patches, collagen, adhesive, thrombin, hydrogel, etc.) that may be beneficial or necessary to aid sealing. The various embodiments of the invention contemplate the use of a variety of devices including, but not limited to patches, plugs, staples, expandable materials, meshes, anchors, sutures, flowable materials, sealants, glues, gels and other wound and tissue repair devices known in the art. To that end, a barrier member may be rigid, compliant, or elastic; furthermore, the barrier member may be a composite of various materials, which are, separately or together, best suited for support and/or sealing functions. Such components may comprise materials inherently radiopaque or they may be treated with substances which make them radiopaque when viewed under any imaging techniques utilized by the surgeon to visualize placement.

Several embodiments of the present disclosure utilize connecting means. The connecting means, connecting member, or connecting element, as the terms may be used interchangeably herein, may be comprised of a number of elements known in, or common to, the art including but not limited to filaments, suture, fabric, threads, ribbon, wire, etc. In a preferred embodiment, the system may be adapted for various types of deployment, such as, portion of the connecting means may be positioned through the tissue that is adjacent to the defect or opening in the annulus. A novel aspect of some embodiments of this invention is a delivery system that has the ability to deliver connecting means through the tissue adjacent to the defect. In some embodiments, a portion of the filament or connecting means may be positioned to extend through the defect or opening in the annulus. In some instances, a portion of the connecting means is intended for passage through the same puncture through which the delivery instruments access the annulus and nucleus tissues. In general, the connecting means can be used in conjunction with one or more of the barrier, sealing, or securement means to aid in the closure and or repair of the defect.

Several embodiments of the present disclosure utilize at least one sealing means. The sealing means, or sealing member, as the terms are used interchangeably herein, may be most beneficial if placed at the outside of the wall of the annulus, though it may also be placed within the wall of the annulus, depending on the geometry of the device, the type of sealing means, and the geometry of the affected anatomy. That being said, the sealing means can be positioned in a number of locations depending on the defect being treated. For example, it may be desirable to have some portion of the sealing means extend into the wall of the annulus and potentially into the NP. Furthermore, the seal may be placed proximal or distal to the fastening device(s). It is recognized that the force internal to the annulus (i.e., the force from the fluid nucleus pulposus) may assist sealing by pressing the sealing means against the annulus, where such sealing means may be preferably located internal to the annulus. The sealing means may be used as a scaffold to help with the repair of the defect. The sealing means may serve as a tissue regeneration guide and may also serve to deliver appropriate agents to the tissue defect.

Several embodiments of the present disclosure utilize at least one securement means, or securement member, as the terms are used interchangeably herein. The securement means may be used in some embodiments to secure the filament and or barrier element at the defect site. The securement means can be stored within the instrument of the invention or added to the device externally and positioned at a location suitable to secure the device. For example, a surgeon can form a knot on the filament portions of several embodiments of this invention and slide the knot adjacent to the tissue defect to secure the device in position. The various embodiments of the invention contemplate the use of a securement means including devices capable of maintaining tension placed on the connecting means or maintaining the desired positions of the device components, including, but not limited to, locking components, knots, plugs, staples, locking washers, slidable components, deformable elements, expandable materials, sealants, glues, gels and other devices known in or common to the art.

Overall disc or annulus geometry may be beneficially altered by placing a device at or through a distal wall of the annulus, while placing a second device at or through the proximal wall, where the devices are connected, e.g., by a tether, suture, flexible, or rigid member. This type of device would allow compression to be placed across each disc wall, while simultaneously compressing or restraining the disc across its diameter. Again, sealing means may be employed, as previously discussed.

These various embodiments may be particularly useful in the situation where the annulus is torn. Since the annulus is fibrous, tears generally occur in the circumferential direction (i.e., not purely radial) along at least a portion of the fibers. Deploying a device across the tear could cause compression to be placed across the torn annulus surfaces, thereby allowing the combination of securement and friction (thereby restricting movement of the torn surfaces against each other) to hold and support the annulus.

Commonly, discectomies or laminectomies are performed to relieve pain. These embodiments may augment, if not replace these types of procedures. That is, multiple fasteners, or a single through-wall fastener, may be placed proximal and distal to the annulus entry tract (in the case of a discectomy), and a sealing patch may be placed adjacent either fastener, or the sealing patch may reside mid-wall to the annulus.

It is also recognized that a sealing member may function as a fastener itself, thereby minimizing the number of device components, procedural steps, and/or procedural time. To that end, a sealing member may be rigid, compliant, or elastic; furthermore, the sealing member may be a composite of various materials, which are best suited for support and sealing functions. As a non-limiting example, such fasteners may be comprised of a rigid polymeric backing material (which may or may not be resorbable, e.g., PLA or polyurethane) which has a layer that contacts the tissue which comprises a malleable material, which may or may not be resorbable (e.g. polymer, collagen, etc.) to seal the tear or procedurally made opening. Such components may be comprised of materials inherently radiopaque or treated with substances which make them radiopaque when viewed under standard imaging techniques to allow the surgeon to visualize placement.

These various embodiments may be at least partially made from permanent or biodegradable materials such as those listed in Table 1, and these devices may have a secondary or tertiary effect by the delivery of drugs or biologics such as those listed in Table 2. In an embodiment of a fastening or sealing device made from the materials described above, once implanted in a living being, the device may cause or induce the new growth or regrowth of cellular material. In this embodiment, the material encourages the ingrowth of cellular material that securely integrates the device into the surrounding tissues, thereby repairing the weakened area in a more effective manner.

In the embodiment where the device is a resorbable material, the ingrowth of cellular material into the device allows for a permanent repair upon complete resorption of the resorbable device, as the material is replaced by the growth of cells to create a natural tissue material similar to and integrated with the surrounding structures.

In the embodiment where the device is a non-resorbable material, the ingrowth of cellular material into the device allows the complete integration of the device with the surrounding tissue, thereby creating a suitable repair having nearly similar compliance and other physical characteristics as the original tissue material.

Several embodiments of the present disclosure utilize at least one elongated delivery means, instrument, or member, as the terms are used interchangeably herein. The elongated delivery means may be used in some embodiments to position or deposit the device components (e.g. barrier, filament, securement element, sealing means, etc.) at a desired location with respect to the defect site. The elongated instrument is suitable for being arranged through the defect or an opening at a location to repair the defect or opening.

In yet another embodiment, the treatment device comprises an elongated instrument, at least one bridging member, and a plurality of connector members. The elongated instrument may be placed in or near the defect, where it is used to deliver the at least one bridging member inside of the intervertebral disc. The elongated instrument may then displace the bridging member from the deployed position, to a position against the inside wall of the disc. This placement should cover at least a portion of the defect. Additionally, the connector members may be deployed from the elongated instrument into tissue at or near the defect and thereby engage the at least one bridging member such that the bridging member is secured against the wall of the disc. This embodiment will afford support to the defect area of the disc.

This embodiment is envisioned to be operative with various other embodiments in the present disclosure. For example, the device may additionally include a fastening element, wherein the fastening element acts cooperatively with the connecting means to secure the bridging element against the disc. Various or all of the members and components of this embodiment may be resorbable, and located or positioned as described elsewhere herein, or by methods known to those in the art.

In certain embodiments the delivery instrument may feature at least one passage element, which may be capable of providing a means for directing or passing at least one connecting member through tissue adjacent to the defect site. A portion of the passage element, passage member, or passage means (e.g. needle), in some embodiments, can be made to temporarily extend from a portion of the elongated delivery instrument into the adjacent tissue for the purposes of passing a portion of the connecting element into the tissue. Preferably, the passage element can then retract into the elongated delivery instrument prior to device removal.

In some embodiments the delivery instrument comprises means for positioning the connecting element(s) into a position for optimal passage through the tissue adjacent to the defect site. The positioning means, positioning member, or at least one positioning element, in some embodiments, can temporarily extend axially from a portion of the elongated instrument, (e.g., into the adjacent tissue) for the purposes of cooperating with the passage element in order to position a portion of a connecting element into and or through the tissue adjacent to the defect. Preferably, the positioning means can be retracted into the elongated delivery instrument prior to device removal.

Procedurally, these various embodiments may be delivered from posterior or anterior directions, based on the anatomical constraints as well as, among other things, herniation, disease, or type and geometry of the defect. While it is envisioned that similar, if not the same, delivery devices and methods may work for posterior as well as, anterior procedures and placements, certain types of procedures may benefit greatly from devices or embodiments which sense their location or detect where they are located in the anatomy. For many annulus repair devices it may be beneficial to utilize minimally invasive methodologies to position the device. Minimally invasive procedures utilize laproscopic or endoscopic instruments to perform procedures through small openings in a patient's skin and can result in less trauma and faster healing times for the patient. However, such approaches are challenging in that the physician may not be able to directly visualize many aspects of the procedure. It has been discovered through experimentation in ex-vivo models that several embodiments of the devices of this invention can benefit by using delivery systems that can locate the transition between the annulus and the adjacent tissues to ensure proper device placement.

Location detection devices are known in the art, for example U.S. Pat. No. 5,282,827, assigned to the assignee of the present disclosure, may be used to accurately place a hemostasis device in an artery (delivery of a hemostasis device using a location detector) also assigned to the assignee of the present disclosure. However, while these aforementioned devices may perform suitably for the currently contemplated procedures, certain modifications could improve their performance. That is, the annulus pulposus, as well as certain of the surrounding fluid, is normally more viscous and less able to flow to provide the "perceptible signal" of the aforementioned patents.

In order to improve upon these previous embodiments, the location detection means incorporated in the current embodiments may further comprise instrumentation or other features allowing for accurate placement of the device percutaneously. Such instruments may be calibrated at some portion so as to allow the surgeon to determine the exact thickness or dimension of the spinal disc component to be traversed with the fixation device. These placement instruments can also be comprised of an actual depth measurement instrument whereby the surgeon can engage the aspect of the disc to which the distal most portion of the device should engage and then determine the traversing distance. A location detection means may also beneficially stabilize the delivery system for the placement of a repair device in an intervertebral disk.

DESCRIPTION OF THE DRAWINGS

FIGS. 4-8, and 11 provide a depiction of the placement of various closure or treatment devices of the present invention.

FIGS. 9 and 10 illustrate various barrier members for use with the present invention.

DETAILED DESCRIPTION OF PREFERRED EMBODIMENTS

Repair of Tears of the Annulus Fibrosis

The annulus fibrosis (AF) of the intervertebral spinal disc is a lamellar configuration of collagen layers intended to maintain the soft viscous internal nucleus pulposus (NP), provide for motion and linkage of the adjacent vertebral bodies (VB). Certain degenerative or pathologic changes may occur either within the NP or the AF which can lead to over stress of the AF and subsequent damage to or tearing of the AF. If left untreated, herniation of the NP may occur through the tear, and most importantly, the herniation may progress posteriorly toward the spinal cord and major nerve roots. The most commonly resulting symptoms are pain radiating along a compressed nerve and low back pain, both of which can be crippling for the patient. The AF may also be torn through traumatic injury, which can lead to progressive degenerative changes and herniation or ultimately listhesis of the adjacent VB.

An embodiment of the present invention is intended to provide means by which the AF can be compressed, e.g., along, or across, as appropriate, the axis of tear, thereby preventing the potential herniation of the NP through the tear and resultant pain.

Figure 1:
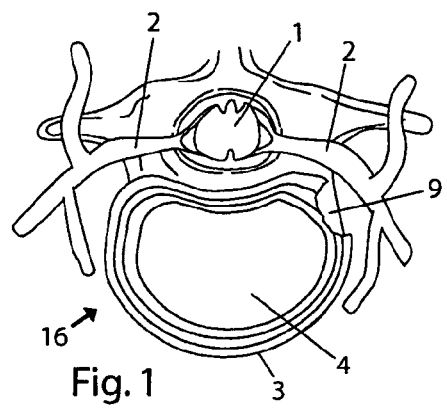
FIGS. 1-3 depict overhead cross-sectional views of a vertebral disc having a defect therein, in the form of an annulus wall having a reduced thickness, a partial tear, and a full tear, respectively.
Figure 2:
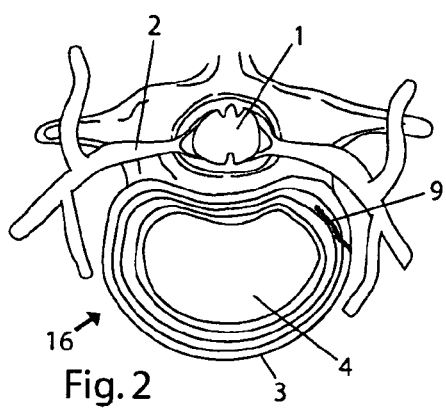
Figure 3:
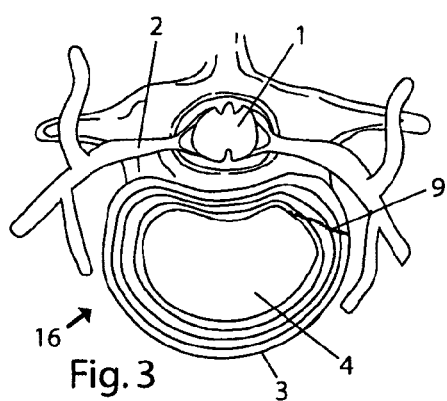

FIG. 1 shows a transverse section of the intervertebral disc space between two adjacent vertebral bodies. The intervertebral disc 16 contains the annulus fibrosis (AF) 3, which surrounds a central nucleus pulposus (NP) 4. Also shown in this figure are the spinal cord 1 and the nerve roots 2. In FIG. 1, the annulus is depicted having a defect 9 therein, wherein the thickness of the annular wall is reduced, as may occur through, for example, a full or partial discectomy procedure, where the removal of at least a portion of the annular wall may be necessary, commonly to minimize the effects of herniated discs. With reference to FIGS. 2 and 3, the defect 9 may be in the form of an annular tear, as depicted by the solid black line through the AF, as may occur in the course of surgical procedures, injury, or natural degradation of the annulus fibrosus. A defect, as used herein, refers to any variation or anomaly from the normal presentation of the annulus, and the term is deemed to include, for example, full or partial tears, full or partial excisions, holes, bulges, degradation, thinning, hyperplasia, or thickening of or in the annulus material. As will be described more fully below, the damage or defect 9 depicted in FIGS. 1, 2 and 3 may be repaired in various manners through the practice of the present invention, for example as can be seen respectively in FIGS. 4-8.

In order to repair these defects, whether full or partial, the device of the present invention may serve to fill the defect and/or apply compression to the annular wall. Furthermore, the present invention may serve to reinforce the defect area, thereby preventing further herniation of tissue (e.g., NP) or the expulsion of nucleus replacement devices or other materials. The defect 9 created by a discectomy procedure may fully penetrate the annulus, extending through to the nucleus pulposus, and forms an opening in the annulus, requiring repair in order to prevent the extraversion of the nucleus.

Figure 4:
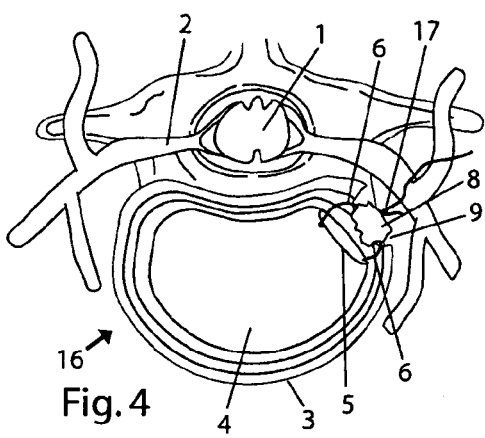
Figure 5:
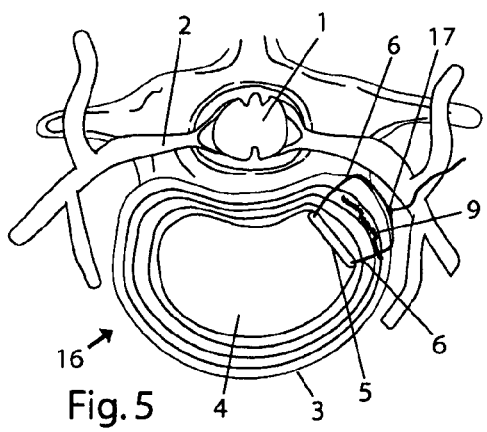

As can be seen by example in FIG. 4, one embodiment of the implanted device consists of a barrier element or anchoring member 5 placed within or near the defect 9 in the annulus, preferably placed against an interior aspect of the annulus such that the barrier overlaps the defect area, thereby covering the defect and extending beyond the defect area. The barrier element is connected to at least one securement element 17 by way of at least one connecting member 6, here depicted as a pair of connecting members 6, thought it is also recognized that additional connecting members and arrangements of the connecting members may be beneficial. The connecting members 6 extend through tissue adjacent the defect 9, or directly through the defect 9 and are affixed to at least one securement element 17. In this manner, the barrier 5 is securely fixed in place against the annulus tissue 3, and is able to effectively seal the opening or defect, thereby preventing the escape of nucleus or implanted material within the nucleus, through the defect 9. The closure of the defect or opening is thereby achieved without requiring the stretching tissue adjacent the defect, where tension applied to the sutures directed through the tissues pulls the tissue faces together to seal the defect. The type of closure, relying on a barrier to cover the defect is better suited for use with the tough tissue characteristics of the annulus.

In some embodiments, at least one sealing member 8 may be deposited within or against the tissue of the annulus, either directly in the defect or near the defect 9, and may serve to ensure an adequate closure of the defect. The sealing member may also be secured with a filament or connecting member 6. The connecting member 6 may preferably be a suture, filament, thread, fabric, or other flexible member. The connecting member may be manufactured from materials known in the art, e.g., synthetic polymers, natural polymers, metal, etc., and may be resorbable or non-resorbable. The barrier 5 may be constructed of a biocompatible material (e.g., polyurethane, resorbable polymer, resorbable collagen or other resorbable or non-resorbable material). The barrier may be rigid as is the case with a polymer or metal anchor, or the barrier may be flexible such as a fabric or other textile such that it may conform to the tissue. The barrier as used in the practice of the present invention may be arranged to serve as an anchoring means for the device, and optionally may serve as a sealing means. The implantable components (e.g., the barriers, sealing members, connecting elements, intermediary components, fastening elements, etc.) of the present invention may be manufactured from a variety of biocompatible, resorbable or non-resorbable, materials, examples of which can be found in a non-exhaustive list supplied as Table 1 below.

In some embodiments of the present invention, as shown in FIGS. 5, 6, 7, and 8, the device is capable of applying and maintaining a compressive force between the outer and inner aspects of the AF 3 at the point where the defect or tear 9 exists, thereby serving as a treatment device to facilitate healing. With reference to FIG. 7 as an example, one embodiment of the implanted device consists of a barrier element 5 placed internally of the annulus, which is connected by way of a connecting member 6 to a sealing element 8, placed externally to the annulus. The connecting member passes through the annulus tissue 3 adjacent to the defect 9 and may preferably be a suture, filament, thread, fabric, or other flexible member. Alternatively, the connecting member may be a rigid member capable of resisting the free movement of associated barrier element or sealing members, and intermediary materials. The rigid connector element may be capable of resisting an encountered force, and also serve to maintain tension upon the tissue restrained by the treatment device. The connecting member may be manufactured from materials known in the art, e.g., synthetic polymers, natural polymers, metal, etc., and may be resorbable or non-resorbable. The barrier 5 may be constructed of a biocompatible material (e.g., polyurethane, resorbable polymer, resorbable collagen or other resorbable or non-resorbable material). The barrier may be rigid as is the case with a polymer or metal anchor, or the barrier may be flexible such as a fabric or other textile to conform to the tissue, in any event, where tension is maintained upon the connecting member 6 against the barrier, the barrier must be able to resist being pulled through the defect or opening in the annulus, and prevent the escape of materials within the annulus through the defect 9.

Figure 6:
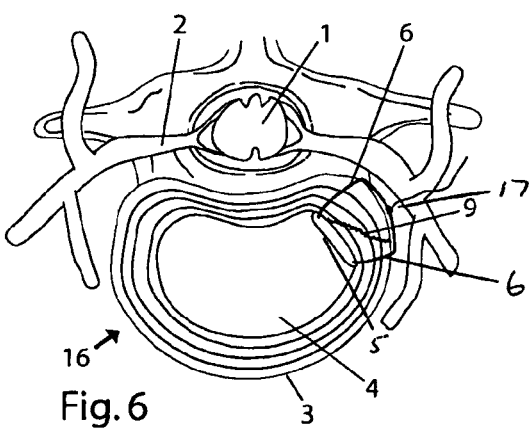

FIG. 6 illustrates one embodiment of the present invention for treating a tear in the annular wall. In a similar fashion to examples already described, a barrier element 5 is placed internally of the annulus, which is connected by way of connecting members 6 to a securement element 17, placed externally to the annulus. In the embodiment shown in FIG. 6, the tension maintained by the placement of the closure device serves to assist with repairing the defect, and or allow for healing to occur, as the compression applied by the device is able to maintain the relative positions of the tissues adjacent the defect.

In another embodiment, as depicted in FIG. 7, a barrier 5 may be placed internally to the annular wall 3, connected to connecting members 6, extending through the tissue adjacent the defect and associated with a sealing member 8. This sealing member 8 may beneficially be a non-rigid material, however, the physical characteristics of the sealing plug are such that it will deform to fill and or conform to the defect 9. A securement element, would preferably be utilized, though the sealing member 8 may also serve as a securement element. For example, the securement element may be in the form of a sealing material that swells or changes conformation upon implantation, such that the connector element may be secured, thereby maintaining the tension or application of compressive force upon the defect.

FIG. 8 represents another embodiment of the present invention for treating a tear in the annular wall, although it is recognized that a full tear, partial tear or other defects could be treated in similar fashion. With reference to FIG. 8, this embodiment of the implanted device consists of a barrier element 5 placed internally of the annulus, which is connected by way of a connecting member 6 to a securement element 17, placed externally to the annulus, and includes sealing member 8 placed within the wall of the annulus 3 and/or within the defect 9. In some embodiments of the present invention, the sealing member 8 may serve to deliver a therapy (e.g. for the purpose of moderating inflammatory response, aiding healing, etc.), such as a biologically active agent, examples of which are listed in Table 2. The sealing member 8 may consist of a flowable or expandable material (e.g. hydrogel, adhesive, packing material, etc.) that serves to aid in sealing or adhering the tissue, so as to prevent the flow of material into or out of the NP (e.g., loss of NP, or inflow of blood, etc.) through the defect 9 in the AF 3 (e.g. a plug). This may be accomplished by providing a sealing member 8 that is able to conform to the shapes and surfaces of the defect 9. It is recognized that the sealing member may be delivered as a rigid material that is able to swell upon being implanted in the body, effectively sealing the defect from the extravasation of nucleus material. The sealing member may additionally feature a natural material that can act as a matrix for cellular infiltration and regeneration of the annulus. The sealing member 8 may also be secured with a connecting member 6' which, in this depicted embodiment, intersects at least a portion of the defect 9. As shown, connecting members 6 extend through the tissue at locations adjacent to defect 9. The connecting members may preferably be a suture, filament, thread, fabric, or other flexible member but may also be a rigid member as described previously. The connecting members 6 and 6' may be manufactured from materials known in the art, e.g., synthetic polymers, natural polymers, metal, etc., and may be resorbable or non-resorbable. The implantable components (e.g., the barriers, sealing members, connecting elements, intermediary components, fastening elements, etc.) of the present invention may be manufactured from a variety of biocompatible, resorbable or non-resorbable, materials, examples of which can be found in a non-exhaustive list supplied as Table 1 below.

As can be seen in FIGS. 9A, B, C and 10 A and B, the barriers may be of any shape or configuration that is suitable for delivery to the defect site and capable of resisting being pulled back through a defect after deployment. The barriers may preferably have several connecting elements attached at various locations of the device. In some instances, as is shown in 9a, 9b, and 9c, several of the connecting elements 6 are located at the periphery of the barrier and these connecting elements 6 are intended for passage through tissue adjacent an annular defect. In these instances, four connecting elements 6 are located at the periphery of the barrier element 5 and serve to anchor the barrier 5 to the tissue adjacent to the defect. It is recognized that any number of connecting elements can be used depending upon the geometry and size of the barrier and defect to be treated. In some instances, for example as shown in 9b, at least one connecting member 6' can be located near the center of the barrier. Portions of these non-peripheral connecting elements 6' are intended for passage either through the defect itself or through the puncture through which the delivery instrument has passed. The barriers 5 may be constructed of a biocompatible material (e.g., polyurethane, resorbable polymer, resorbable collagen or other resorbable or non-resorbable material). The barrier may be rigid as is the case with a polymer or metal anchor, or the barrier may be flexible such as a fabric or other textile as described previously. The barriers may be rectangular in shape as shown in FIGS. 9A and 9B, circular/oval as shown in 9C, or any desirable shape. The barriers may also be formed into 3-dimensioanl structures to help them best seal and repair the defect. As shown in FIG. 9C, the barrier may be comprised of a flexible membrane 50 (e.g. polyurethane mesh, collagen sheet, etc.) and a reinforcing expandable membrane 52 (e.g. nitinol wire, polymer ring, etc.). The barrier of FIG. 9C is suitable for being collapsed and stored within the elongate delivery instrument and, upon delivery into the area adjacent to the defect, the reinforcing membrane 52 causes the barrier 5 to resume its original oval shape so that is may conform to the defect site. As shown in FIG. 9C the barrier may be attached to several connecting elements 6, in this case 4.

Figure 10A:
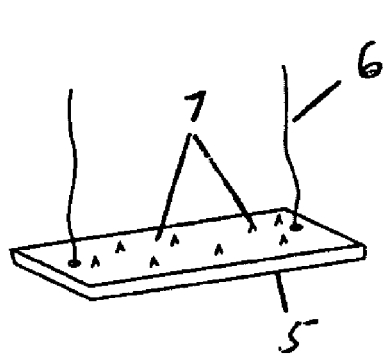

As illustrated in FIG. 10A, the barrier 5 may also contain small barbs or points 7 to interface with the internal or external surface of the AF or surrounding tissue to aid in securing the device and prevent it from being dislodged.

Figure 10B:
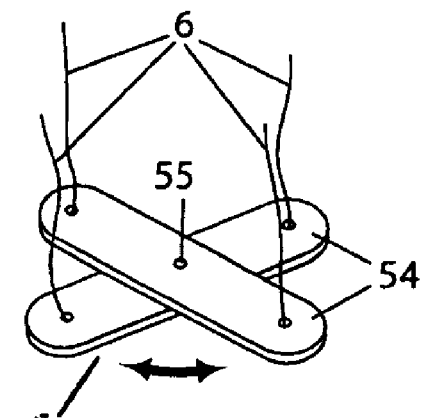

As illustrated in FIG. 10B, the barrier may consist of multiple barrier elements that once deployed are able to seal the defect and/or resist being pulled through the defect. The device of FIG. 10B is suitable for being collapsed and stored within the delivery instrument in a first conformation, and upon delivery into the area adjacent to the defect, barrier may arrive at a second conformation, for example, the elements 54 of FIG. 10A can pivot at location 55 and expand into the barrier 5 of cruciform shape shown. It is recognized that barriers 5 may be specifically shaped for a particular purpose, that is, barriers intended to be inserted into the interior of the annular wall may have a first orientation, shape, or curvature, while another barrier intended for use outside of the annular may feature a second orientation, shape or curvature.

It is also recognized that various arrangements of barriers and connecting members may be necessary. For example, it might be beneficial to utilize a single barrier on the exterior of the annulus, and place a plurality of barriers in the interior of the annulus, all connected by at least one connecting member, or alternatively, the arrangement may be reversed, with a single interior barrier and a plurality of exterior barriers. It is recognized that the barriers described above may additionally feature some application (e.g. coating) of a sealing material (to be discussed below) to aid in maintaining annulus integrity against leakage. The barriers, or other members, may also contain a marker, additive, or other material that can be visualized with x-ray or other imaging technologies to assist with the placement of the device and potentially allow for longer term follow-up of the device location.

The materials of the present invention that are resorbable may comprise a porous tissue matrix material (PTM). This PTM material will preferably have an interconnected porosity, and sized to encourage the invasive growth of new cellular material. The interconnected porosity also serves to ensure adequate fluid flow to provide an optimal growth environment for the invasive cells. The ingrowth of new cellular material will beneficially encourage the incorporation of the device material into the nearby tissues, and provide for biomatching or compliance matching, where the device material and components present similar physical characteristics as the original tissue.

Figure 11:
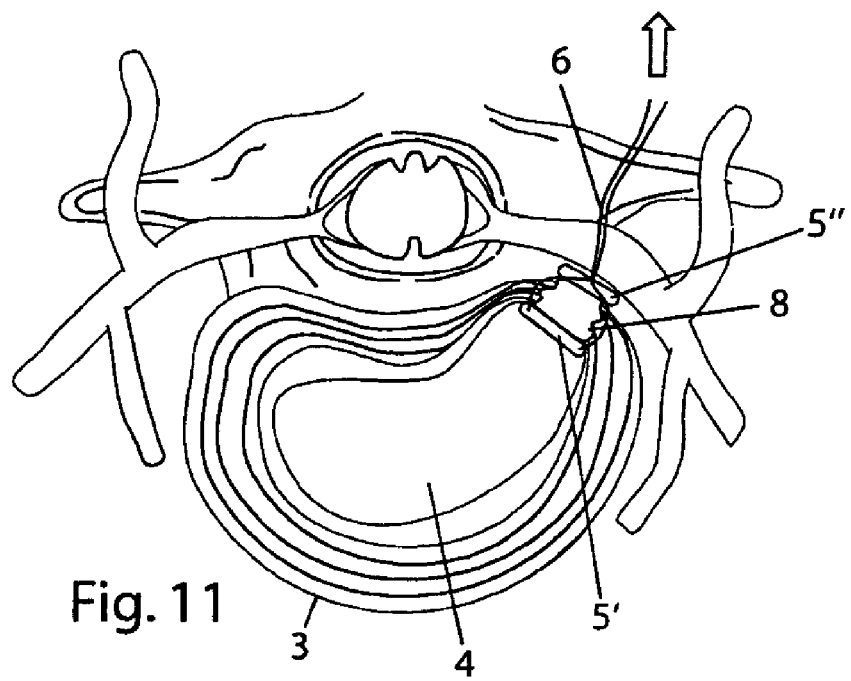

Referring to FIG. 11, where the defect 9 extends fully through the annular wall, and may be created, for example, as a consequence of a full discectomy, the intermediate or sealing component 8 is preferably capable of filling the entire defect void created by the removal of a portion of the annulus. The sealing member 8 may be locked in place, and against adjacent walls of the annulus by an applied pressure created through compression applied through the connecting member 6 and external barrier member 5".

Figure 12:
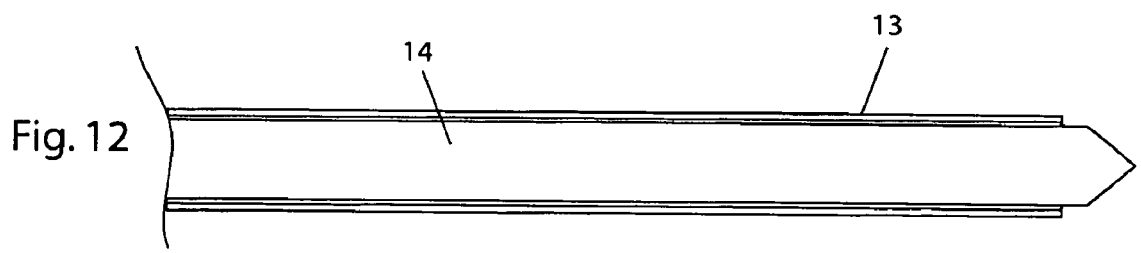
FIG. 12 is a cross sectional depiction of a cannula and obturator for the implementation of the present invention.

In practicing the present invention for the repair of a partial or full defect in the annular wall 3, an access sheath (e.g. a cannula, solid probe, rod, needle, etc.) 13 or series of sheaths, optionally housing an obturator 14, as depicted in FIG. 12 may be inserted through a percutaneous incision in the external skin and extended through underlying tissue to the AF using techniques known in the art. It is recognized that in some circumstances, a series of sheaths may be used to gradually dilate an access tract to, and in some instances, through the defect. If desired, a final sheath 13 can be left in place, through which the delivery instruments of this invention can be positioned. Guide wires or other similar elements can be used to guide the delivery instrument to the defect site, through techniques common in the art.

In an embodiment, the access sheath 13 through which any subsequent instruments or components may be inserted is preferably of a fixed length. The subsequent instruments which may be directed through the sheath may incorporate that fixed length into their shafts, and extend out the distal end of the sheath by a precisely determinably amount, as they may be calibrated or have markings, in order to allow the surgeon to determine the depth of penetration into the target tissue (e.g., into the disc, thickness of the annulus, and zone of nucleus). As the sheath and obturator are directed to the target site, the obturator may be removed and a trocar or tissue dilator (for example, tissue dilator 18 of FIG. 21) is used to initially penetrate into the annulus fibrosis (AF) at the zone of the defect or tear. A sharp trocar or tissue dilator (which is preferably calibrated along at least a portion of its length) may be inserted through the access sheath 13 to the surface of the AF at the location of the tear and confirmed in some manner (e.g., via radiography). It is envisioned that multiple increasing diameters and/or lengths of trocars or tissue dilators may be used to gradually open a lumen within the AF. The instruments inserted into the living being, (e.g. the sheath, trocar, and obturator, etc.) may feature monitoring elements (e.g., radiopaque markers, bands, penetration markers, orientation markers, calibration, etc.) to allow accurate tracking, placement and implementation of the devices using techniques known in the art (fluoroscopy, x-ray visualization, etc.). The trocar may then be advanced into the disc, for example through the AF to the level of the NP. The trocar may then be removed, thereby creating an accessible open lumen within the cannula or access sheath 13, such that the elongate delivery device 15 of FIG. 13, shown here in cross-section containing an embodiment of the treatment device, may be inserted into and extend through the access sheath 13 as depicted in FIG. 14.

Figure 13:
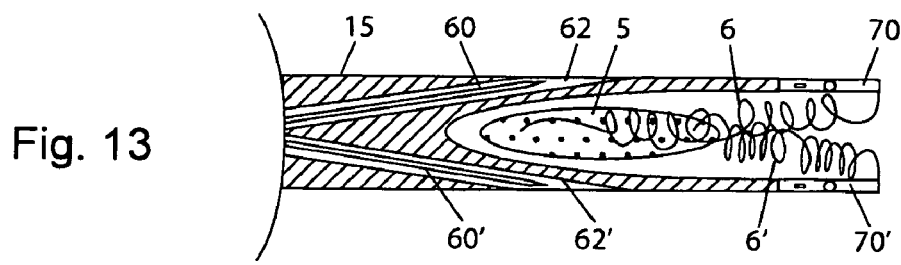
FIG. 13 is a partial cross-section of embodiments of the delivery device and portions of the treatment device of the present invention.

As illustrated in FIG. 13, one embodiment of the treatment device or closure device includes a distal barrier 5 attached to at least one connecting elements 6 and 6'. The barrier element 5 depicted here is in the form of a flexible mesh-like material capable of being collapsed and stored within the distal portion of the delivery instrument 15 for later ejection into the wound area for placement adjacent the opening or defect upon deployment. In another embodiment, a sealing element may be included as an intermediary component that is located contiguous with the connecting members 6' and/or 6, and adjacent the barrier element to facilitate the filling of the defect upon delivery. Also shown in FIG. 13 are passage means 60 and 60', which are stored while recessed, in channels 62 and 62', respectively, in the body of the delivery instrument 15. As will be described later, the passage means 60 and 60' in this embodiment can be extended out of the distal portion of the channels to pierce the tissue surrounding the defect. As will also be described later, the passage means are used to pass the connecting element(s) through the tissue adjacent to the defect. The device may have one or more passage means, optimally the device would have at least two. Also shown in FIG. 13 are positioning elements 70 and 70'. The positioning elements are deployed to position a portion of the connecting member 6 and/or 6' to a location where the passage means 60 and 60' can cause the connecting members 6 and 6' to pass through the tissue adjacent the defect. As will be described, the positioning elements can expand laterally, and preferably radially from the elongate delivery instrument 15 such that when passage elements 60 and 60' are no longer recessed in channels 62 and 62', but instead extend distally from the body of the elongate delivery instrument 15, the passage means will intersect with the desired portion of the connecting members 6 and 6'. Preferably, the passage means 60 and 60', will interlock or become attached to the connecting members 6 and 6' upon intersecting, and as the passage means are retracted, they will draw a portion of the connecting members with the passage means, thereby directing at least a portion of the connecting members through the tissue adjacent the defect.

Figure 14:
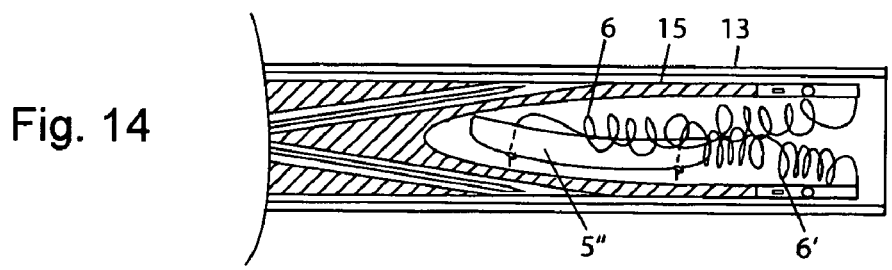
FIG. 14 is another embodiment of a treatment device and the delivery device, housed within the access sheath.

FIG. 14 depicts an alternative embodiment of the delivery device 15 within the access sheath 13, and is prepared for being introduced into the disc through percutaneous puncture, and extended into an aperture created in the AF to the level of the NP for delivery and implementation of the remaining components of the device (e.g. the closure device elements). FIG. 14 depicts an alternative form of a barrier element 5", wherein the barrier element 5" is fabricated from a more rigid material such as nylon, PLGA, etc. In this embodiment, the delivery device 15 may be calibrated along its proximal end relative to the proximal edge of the access sheath 13 to allow the surgeon to determine when the barrier element 5' has traversed a distance approximately equal to the thickness of the AF. Alternatively, other location detection mechanisms may be utilized in ensuring accurate placement of the delivery device for placement of a fastener or closure device.

With reference to FIGS. 13 and 14, the delivery device 15 may be shaped or incorporate elements that deploy the device components (e.g. barrier element 5, sealing element, etc.), such as a tamping or ejecting mechanisms, or a rod that can be extended down through the elongate delivery device 15 to eject the closure device elements, such as the barrier, as may be necessary.

Figure 15:
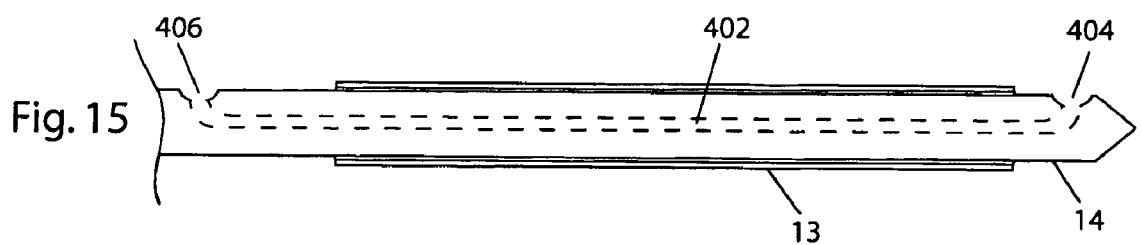
FIG. 15 illustrates a cannula and access sheath of the present invention incorporating a location detector means.

In this or other embodiments, the use of a means for location detection may be beneficial. In FIG. 15 there is shown embodiment of a locating device for effecting the proper positioning of the access sheath 13 or other deliver device within the annulus or nucleus. As can be seen in FIG. 15, the depicted embodiment of a locating device basically comprises a conventional obturator 14 providing a passageway 402 extending longitudinally down substantially the length of the device, preferably internal to the obturator, although external may be capable of functioning similarly. In the embodiment having an internal passageway lumen 402, a detection port 404 extends radially inward into the device communicating with the distal end of the passageway 402, while a proximal port 406 extends radially inward into the device communicating with the proximal end of the passageway 402. The locating device is arranged such that it may be fully inserted within the access sheath 13 and extend a precise amount beyond the end of the access sheath, as shown in FIG. 15, and further the proximal port does not enter the proximal end of access sheath 13, thereby ensuring that proximal port 406 remains accessible or visible to the operator.

The length of the annular passageway 402 is selected so that when the obturator 14 of the locating device shown in FIG. 15 is fully extended within the access sheath 13 and the distal end of the sheath is located within the interior of the annulus or lumen, the detection port 404 of the passageway 402 extends just beyond the free end of the sheath, while the entrance port 406 is accessible to the operator. The detection port 404 forms a window, which is exposed to the material in the annulus.

In another embodiment of the location detector of FIG. 15, a flexible or reconfigurable member (e.g. a probe)(not shown), may be inserted into proximal port 406 and extended through the passageway 402, exiting at detection port 404, such that the flexible probe or member may be used to probe the tissue, thereby using, for example, tactile feel to locate the sheath or other insertion member, such that a device may subsequently be accurately placed.

In another embodiment of a location detector, sensors (not shown) may be placed at or near the distal end, such as within detection port 404 to confirm accurate placement. Such sensors may be in the form of, for example, optical sensors or pressure sensors that may be exposed to the tissue or fluid during placement of the device, and generate an indicator signal or other feedback for the operator and enable confirmation of accurate placement of the device.

Description of an Exemplary Procedure for Repair of a Defect in the AF Using the Device of the Present Invention With reference to FIG. 3, there is depicted a typical defect 9 in a vertebral disc 16, here shown as a full tear in the annulus 3. In the practice of the present invention, various techniques known in the art may be utilized for the introduction of the closure device through a delivery device in order to repair such a tear in the annulus. The following description of one delivery technique is for example only, and is not intended to limit the inventor to only this practice, as other similar or equivalent delivery techniques are available and known in the art, and the practice of the present invention through these equivalent procedures is inherent within the description.

Figure 16:
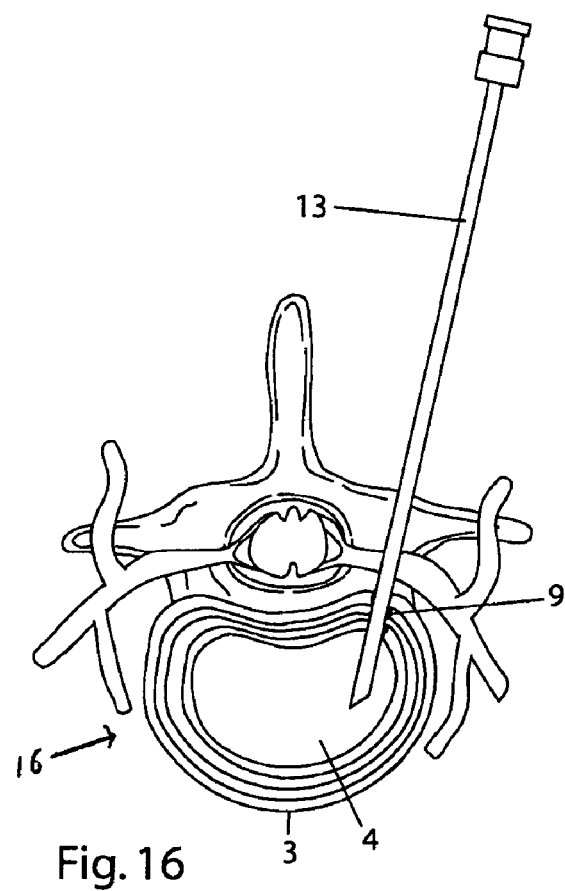
FIG. 16 An access cannula (e.g. needle) positioned into the defect of FIG. 30.
Figure 17:
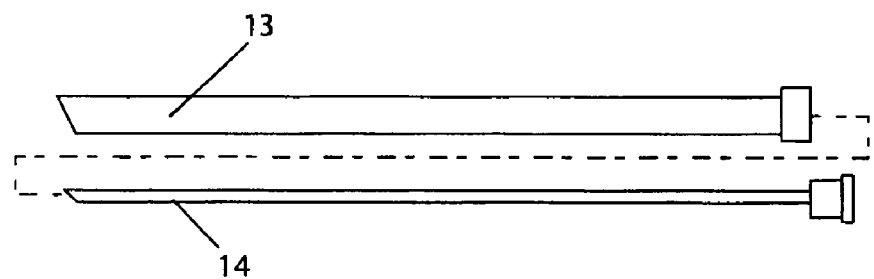
FIG. 17 depicts an exploded profile view of a cannula and obturator.
Figure 18:
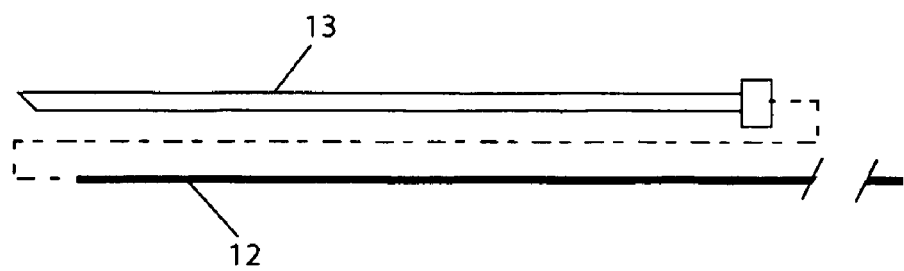
FIG. 18 shows an exploded profile view of a guidewire and cannula.
Figure 19:
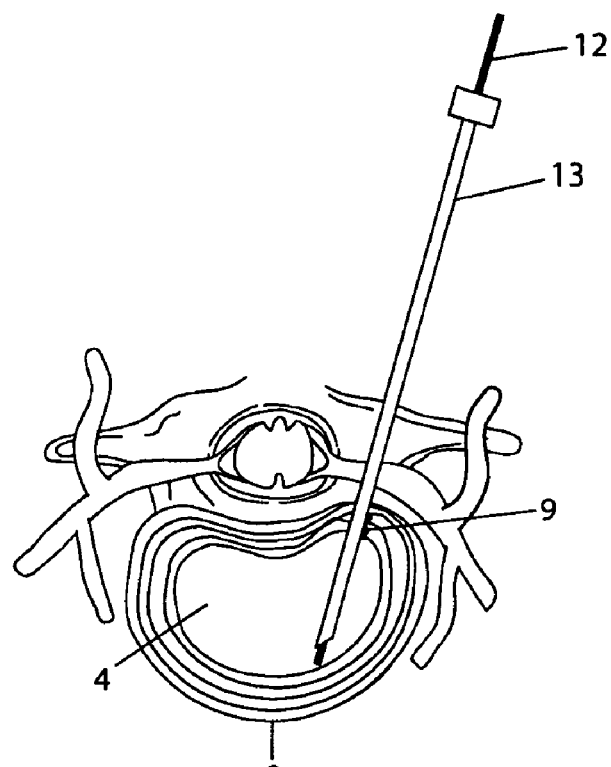
FIG. 19 shows an elevated view of the guidewire positioned into the access cannula and directed into the disc of FIG. 16.

As depicted in FIG. 16, an access cannula 13 (e.g. a needle) may be positioned through a defect 9 in the annulus 3, and the needle extended into the interior of the annulus (i.e. the nucleus pulposus 4) using standard techniques known in the art, preferably radiographic techniques (e.g. x-ray). As shown in the exploded view of FIG. 17, the cannula 13 may initially have an obturator 14 as shown, which may serve to prevent tissue from entering into the central lumen of the cannula while it is being directed through tissue. Upon insertion of the cannula 13 into the interior of the disc 16, the obturator 14 may be removed, leaving an empty lumen in the cannula 13 for the introduction of the delivery device, as will be discussed. Alternatively a guidewire 12 or other wire-like element may be introduced into the cannula (as can be seen in exploded form in FIG. 18, and in place in FIG. 19). The use of a guidewire 12 will allow the replacement of the first inserted cannula or access sheath 13, to be replaced with another access sheath suitable for passing the elongate delivery device therethrough (to be discussed) that may be advanced along the placed guidewire 12.

Figure 20:
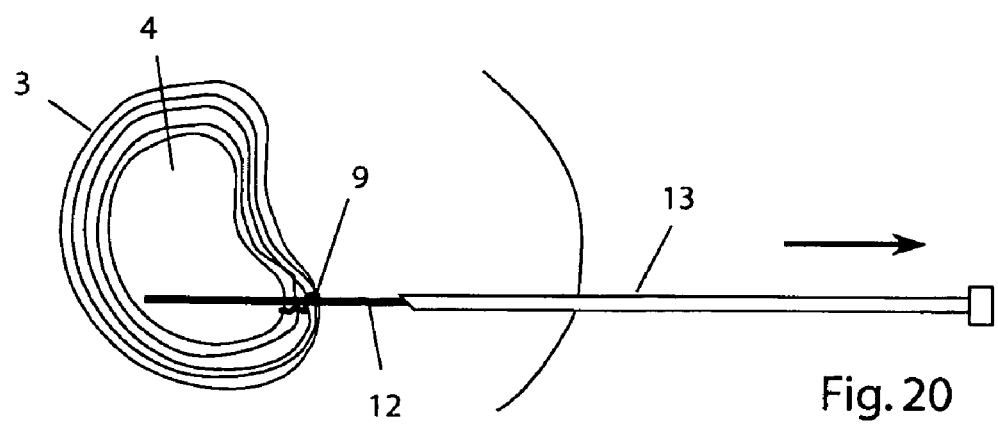
FIG. 20 shows an elevated view of the guidewire of FIG. 19 remaining in place as the access cannula is removed from the patient.
Figure 21:
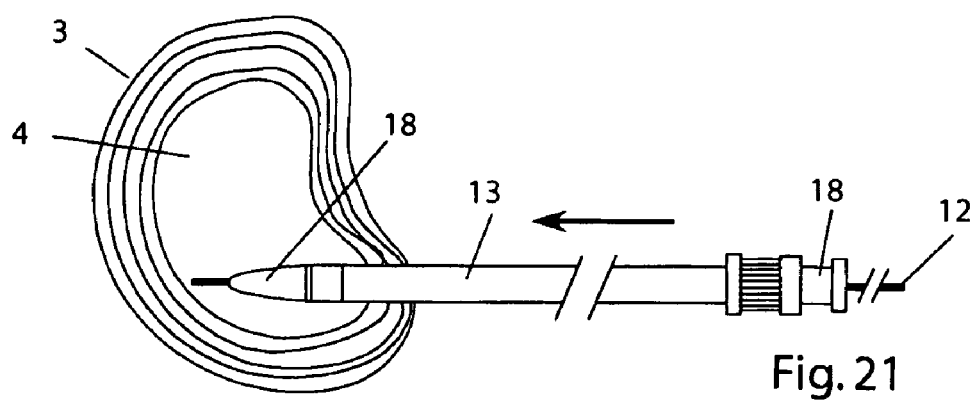
FIG. 21 shows an elevated view of the positioning of an Access sheath over the guidewire of FIG. 20.

With reference to FIG. 20, after removal of either or both of the obturator 14 (from FIG. 17) or the cannula 13 (from FIG. 19), the guidewire 12 or wire-like element can be left in the puncture or defect 9 and may serve to guide access sheath 13 suitable for use with the delivery system of the present invention (e.g., delivery system 15 of FIG. 13 or 14) to the appropriate position at the target site. As depicted in FIG. 21, the access sheath 13 may optionally utilize at least one tissue dilator 18 (e.g. trocar, obturator, etc.) that is arranged to expand the initial opening or defect 9 in the annulus 3 to a size capable of allowing the penetration of the access sheath 13, and associated elongate delivery device 15 housing a closure device into the opening created. It is recognized that a series of tissue dilators 18 and or access sheaths 13, increasing in size may be utilized to achieve an aperture of greater size in the tough annulus layer 3 than the original opening or defect 9 created in FIG. 16. In use, the tissue dilator 18 is inserted through the access sheath 13, and extends distally therefrom, forming a tapered snout that serves to expand the tissue, such as in annulus 3, to the point where the access sheath 13 suitable for use with the delivery device 15 may be inserted.

As the access sheath 13 is positioned over the guidewire 12 and advanced into the aperture, as seen in FIG. 21, various techniques for ensuring the positioning of the device are available. For example, radiopaque markers (not shown) can be used to properly locate the sheath at the ideal position. Alternatively, other location detector mechanisms, as described previously or known in the art, may be utilized.

Figure 22:
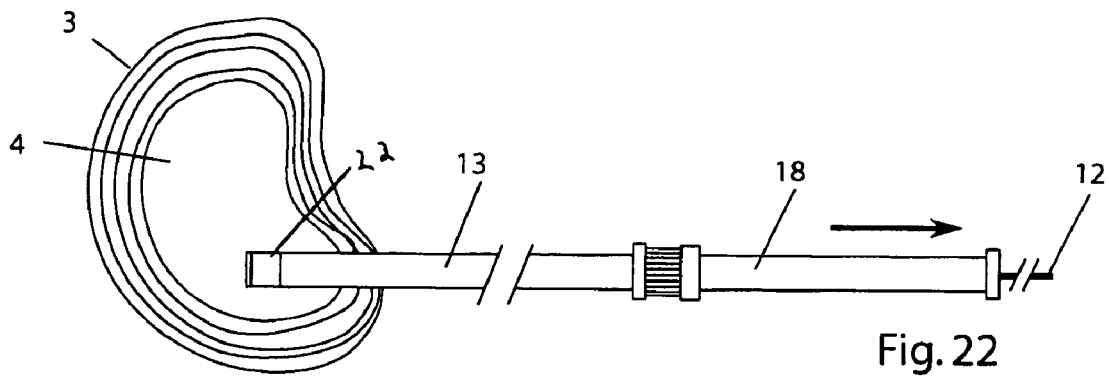
FIG. 22 shows an elevated view of the Access sheath of FIG. 21 as the obturator (e.g. dilator) and guidewire of FIG. 21 are removed.

In the embodiment where an access sheath 13 incorporates an expandable or reconfigurable locking member 22, as can be seen with reference to FIGS. 22-26, located at or near the distal end of the access sheath 13, the locking member 22 may also function as a location detector. In this manner, the actuation of the expandable or reconfigurable locking member may provide feedback or tactile sensations to the operator as to the type of tissue is being encountered, thereby allowing the operator to distinguish placement within the annulus 3 from placement within the nucleus 4. For the practice of this embodiment, it is preferred that the tissue dilator 18 and wire 12 be removed, as depicted in FIG. 22, leaving the access sheath 13 penetrating into the disc 16.

Figure 23:
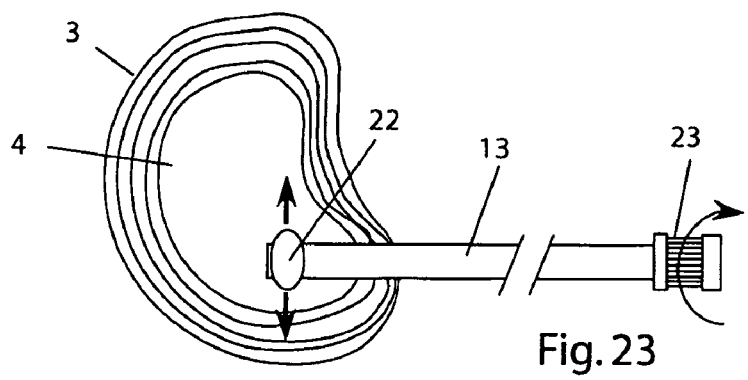
FIG. 23 shows an elevated view of the activation or deployment of a location detector on the access cannula of FIG. 22.

As shown in FIG. 23, actuation mechanism 23 is used to deploy or reconfigure the locking mechanism 22 to provide location detection. The actuation of the expandable or reconfigurable locking member 22 may be accomplished by various means (e.g. inflation, or mechanical actuation). As shown in FIG. 23, with this particular embodiment, actuation mechanism 23 is preferably located at the proximal end of the access sheath 13, and may be rotatable, and upon rotation, or in the case of an inflation port, upon delivery of an inflation charge, serves to actuate the locking member 22 at the distal tip of the sheath 13, causing the locking member 22 to expand via one of several mechanisms (e.g. balloon expansion, nitinol wings, etc.). In the instance where the actuation of the locking member 22 were to cause the locking member to encounter tough annulus tissue, this would serve as an indicator to the operator that the sheath must be advanced into the nucleus, until softer nucleus material is encountered, allowing easier expansion of the locking member 22. The mechanisms (e.g. balloon, nitinol wings, etc.) may also be used to prepare a physical space for the delivery of the device. For example, the balloon can be inflated to a large initial diameter to stretch or otherwise move tissue. Then the balloon can later be reduced in size to provide a deployment space for a component of the device (such as a barrier or sealing member). In the case of an embodiment having another expandable mechanism, such as nitinol wings, the expandable mechanism may be expanded and optionally through the rotation or translation of the access sheath, or other instrument upon which the mechanisms are mounted, a physical space can be created to allow for proper deployment of the remaining components of the device.

Figure 24:
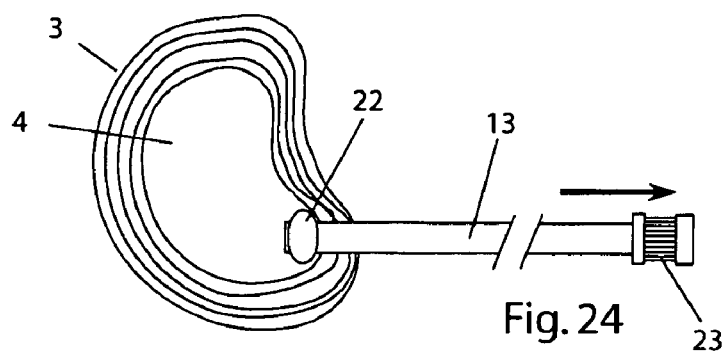
FIG. 24 shows an elevated view of the retraction of the access sheath and deployed location detector of FIG. 23.
Figure 25:
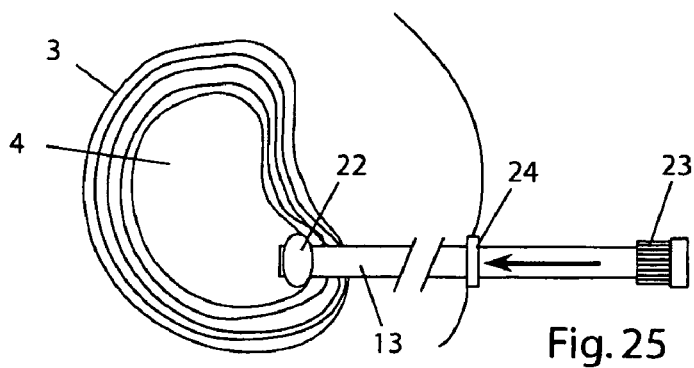
FIG. 25 shows an elevated view of a deployment of a locking ring on the access sheath of FIG. 24.

With reference to FIG. 24, the operator or surgeon may retract the access sheath 13 until the desired location is achieved using a location detection means as described preciously. Resistance may be felt as the locking member 22 first traverses relatively freely through a portion of the nucleus 4 and subsequently encounters the tougher annulus 3 tissue, thereby providing the resistance to further retraction. Optionally, and as shown in FIG. 25, a locking mechanism (e.g. a locking ring) 24 may be advanced down the access sheath 13 in a proximal to distal fashion toward the puncture (i.e., against the skin or tissue of the patient) to stabilize the access sheath 13.

Figure 26:
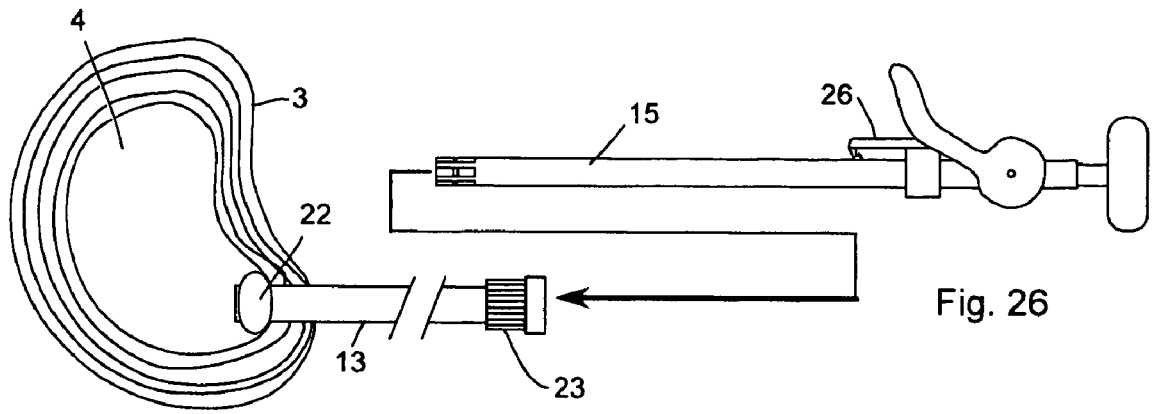
FIG. 26 provides an elevated view of the access sheath of FIG. 25 and depicting the introduction of the delivery system into the access sheath.

As shown in FIG. 26, the elongate delivery device 15 containing the closure device of the present invention may now be inserted into the access sheath 13. In a preferred embodiment, the anchoring or barrier element 5 is contained within and in place at or near the distal end of the delivery device 15 (as described previously with reference to FIGS. 13 and 14), and is temporarily maintained in alignment with the axis of the access sheath 13 to allow passage into the sheath 13. It is also contemplated that the delivery device 15 could be introduced into the defect without the use of an access sheath. The delivery device 15 could be modified to include a passageway that would permit it to be guided into the defect site over a guide element 12 (e.g. guidewire, k-wire, etc.). The delivery device 15 could also include a rounded or more atraumatic tip to assist with passage through the tissue.

Figure 27:
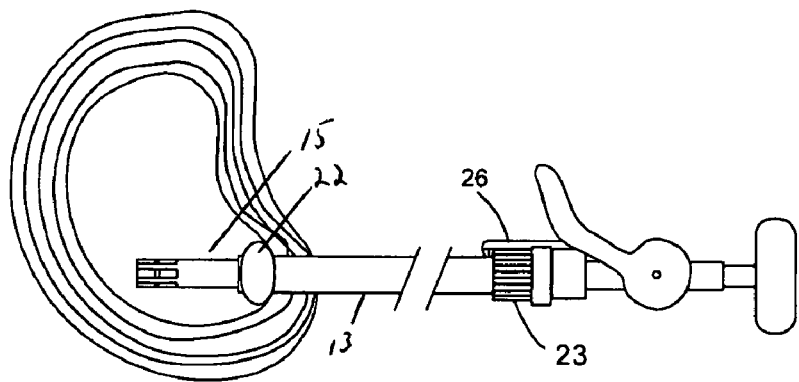
FIG. 27-32 depict elevated profile views and illustrations of the deployment and securement of the closure device of the delivery system of FIG. 26.

As shown by FIG. 27, upon full insertion of the delivery device 15 into the access sheath 13, the distal portion of the device 15 extends beyond the access sheath 13. Also with reference to FIG. 27, a locking tab 26 may be incorporated onto the proximal end of the delivery device 15. As the delivery device 15 is fully inserted, the locking tab encounters the access sheath 13. The locking tab 26 is capable of one-way movement over the access sheath's 13 proximal end, and will then become engaged with the access sheath such that the access sheath 13 and the delivery device 15 are now interlocked as one unit.

Figure 28:
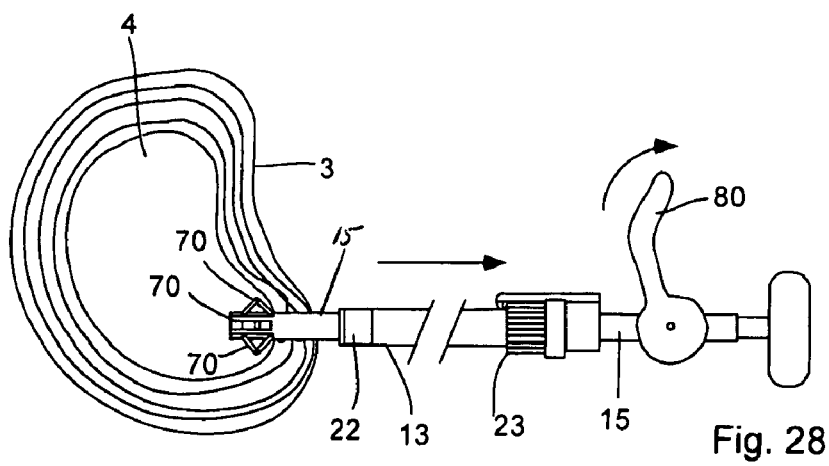

As shown in FIG. 28, the expandable or reconfigurable locking member 22, located at or near the distal end of access sheath 13, may be de-actuated, such as through the action of actuation mechanism 23, such that it reverts back to its original, non-expanded state.

Also as shown in FIG. 28, activation of a secondary actuation mechanism (e.g., lever) 80 causes the deployment of positioning elements 70 at the distal portion of delivery instrument 15. As described previously, the delivery device may have any number of positioning elements 70 as is necessary for the application. The positioning elements may extend in one axis, presenting a pair of positioning elements upon actuation. Alternatively, several positioning elements (e.g. 3 or more) may be simultaneously deployed to form a flange or series of protruding elements extending laterally from the body of the delivery device 15 in many axis or orientations.

If desired, the access sheath 13 and delivery device 15 can be withdrawn as one unit to a desirable location as is necessary. For example, as shown in FIG. 28, delivery device 15 and access sheath 13 are withdrawn as one unit from the defect until the laterally deployed positioning elements 70 contact the interface between the annulus 3 and the nucleus 4. In this embodiment, positioning elements 70 may also be capable of functioning as a location detector in a manner similar to that previously described with reference to the expandable locking member. In this manner, the actuation of the expandable or reconfigurable positioning elements may provide feedback or tactile sensations to the operator as to the type of tissue is being encountered, thereby allowing the operator to distinguish placement within the annulus 3 from placement within the nucleus 4.

Figure 29:
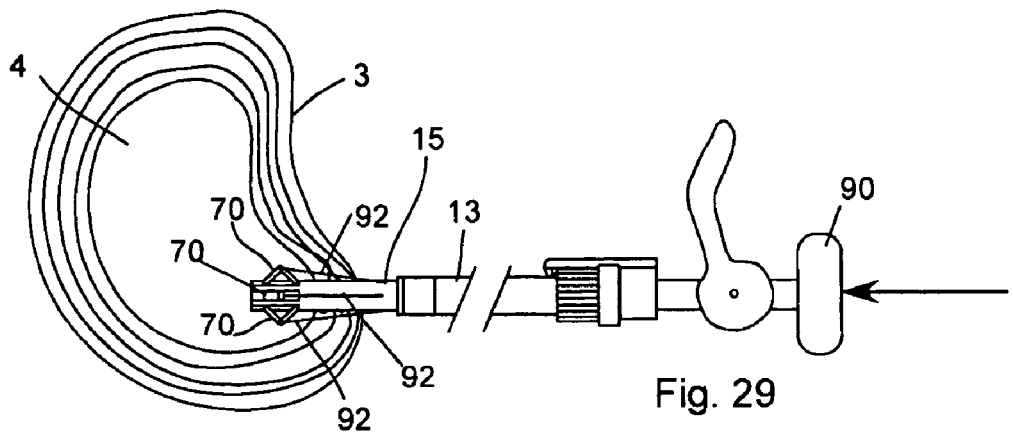

As shown in FIG. 29, activation of plunger 90 causes the deployment of passage elements 92 from the distal portion of delivery instrument 15. As described previously, the device 15 may have any number of passage elements as is necessary for the application. The passage elements can be constructed and configured to readily pierce through the tissue that is adjacent the delivery instrument (e.g., a needle). Each passage element 92, upon deployment in response to activation of plunger 90, is arranged to intersect a respective positioning means 70 and thereby engage the connecting members 6 associated with each positioning means. The engagement of the passage means and the connecting member may be accomplished in a manner that ensures the secure, one-way, connection between connecting member 6 and the respective passage element 92.

Figure 30:
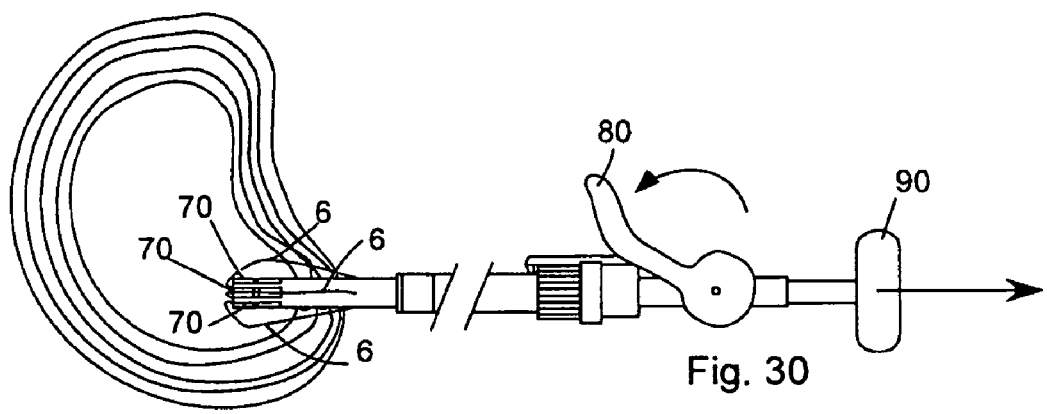

As shown in FIG. 30, plunger 90 may then be retracted, thereby withdrawing the passage means 92 back through the tissue, and into the recessed channels of the delivery instrument 15. The retraction of the passage elements 92 causes the securely attached connecting elements 6 to pass along the same passage, through the tissue adjacent to the delivery instrument and enter into the recessed channels of the delivery instrument. After complete retraction of the passage elements, a portion of the connecting elements remain within the internal lumen of the delivery device, attached to the remaining components of the fastener, and another portion of the connecting element (e.g., a filament) is extended along the passage created by the deployment of the passage means, and attached to the passage means contained within the recessed channels of the delivery device. Secondary actuation mechanism 80 may then be deactivated, thereby collapsing the positioning elements 70 back to their original, more compact state.

Figure 31:
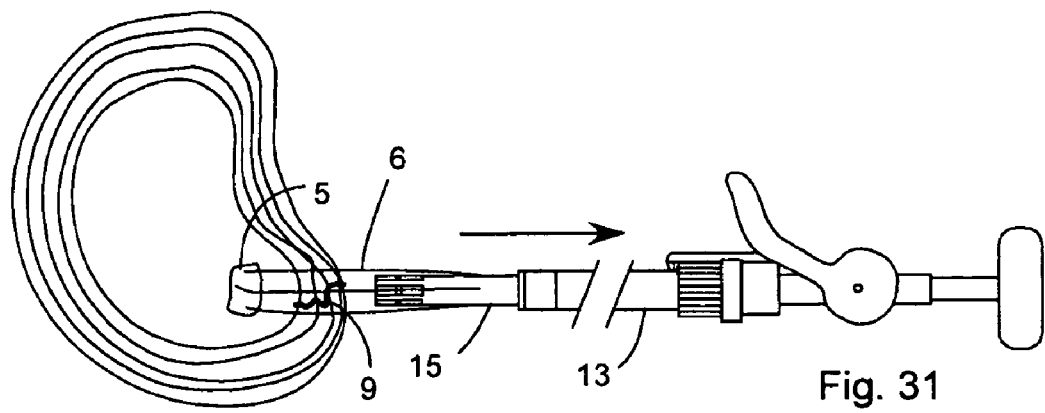

As shown in FIG. 31, the delivery instrument 15 and access sheath 13 can be withdrawn form the defect site as one unit. Upon withdrawal of the delivery instrument 15, the components of the fastener may now be deployed; barrier member 5 is deployed from the distal portion of delivery instrument 15 and the continued withdrawal of delivery device draws the connecting elements through the tissue that is adjacent to the defect 9. Tension upon the fastener components (e.g., barrier member, sealing member and connector elements, etc.) may be maintained through the at least one connector element 6 by the retraction of the delivery device 15, and the resistance of the barrier member 5 as it encounters thicker nucleus tissue or tough annulus tissue, as depicted in FIG. 32.

Figure 32:
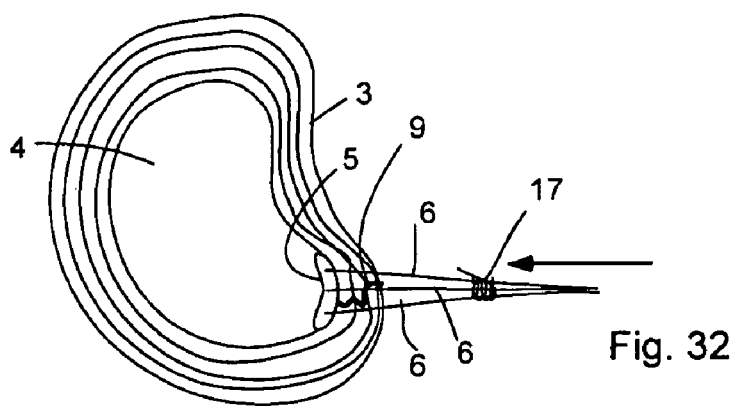

As further depicted in FIG. 32, connecting elements 6 can be placed in tension, such as being pulled taught, by continued withdrawal of the delivery instrument, and securement member 17 can be advanced along the connecting elements 6 to a desired position to secure the barrier member 5 and the connecting members 6 at the desired location to help approximate and or treat the tissue contiguous to the defect site 9. Subsequently, excess connector element may be removed, or trimmed to minimize the opportunity for complications as healing occurs (e.g., infection, irritation, scarring, etc.).

The securement element 17 may be positioned, in one embodiment, against the outside of the puncture in the annulus 3, and internal to the patient. Alternatively, the fastening element 17 may be placed outside of the patient and against the skin where the connector element enters the tissue. The securement element 17 can be any of a variety of tension maintaining devices, for example, a locking washer, a knot, or a variety of elements or combination of elements may be utilized. The securement element 17 could be pre-stored within the delivery instrument 15 or it could be added to the connecting members 6 by the physician during the procedure. Further, a small-elongated tamper tube or other instrument may be utilized to push down or advance the securement element 17. The tube is preferably removed after securing the securement element 17. Alternatively, a pulley configuration could be used with a securement element 17 in the form of a sliding locking knot, and would not require the use of an elongated tube to apply tension, as the operator applies tension simply by pulling on the connector element 6, whereby the pulley arrangement and sliding locking knot are arranged to maintain that tension. Glue or some other sealant or adhesive could also be used to secure the device at the desired location.

Various embodiments of a closure device can be utilized in the practice of this invention, as have already been described. As depicted earlier in FIG. 4, a sealing member 8 associated with a portion of the flexible connecter element 6 may be deposited within the tissue as desired. With this embodiment, continued retraction of the access sheath 13 and delivery device 15 results in the deployment of the sealing member within the annulus tissue 3. Altering characteristics necessary for the various embodiments of the closure device, such as manipulating the length of the connector element 6, and varying the placements of the access sheath 13 can achieve the deployment of the various described embodiments of the closure device.

After the closure device is fully positioned at the tissue defect 9, any extraneous connector element 6 or suture may be removed. As appropriate any of the embodiments of the device described in the specification may be used to deliver various medications at the puncture site and to the surrounding tissues. The delivery of such medications may be accomplished as a coating of drug delivery material associated with one or more of the fastener or device components, such as the barrier or anchor, sealing member, connector means, etc. It is also recognized that these or other components of the device may be manufactured from a resorbable material to deliver biologically active agents as the components bioerode, thereby forming a depot. A non-exhaustive list of examples of drugs or biologically active agents is provided in Table 2.

Repair of Herniated or Bulging Annulus Fibrosis

Figure 33:
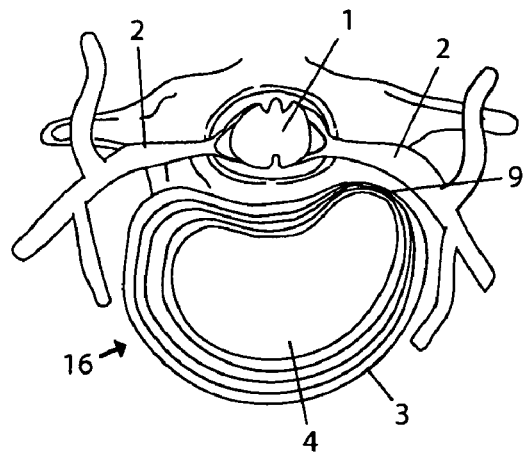
FIGS. 33 and 34 show overhead cross-sectional views of a vertebral disc having a defect therein, in the form of a hernia or bulge in the annulus, having an intact annulus or extravasation of the nucleus.
Figure 34:
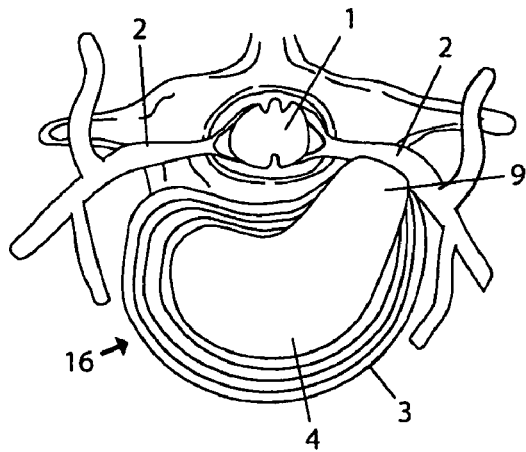

An annular defect such as a bulge or herniation may be caused by or be the result of weakening in the AF secondary to physiologic changes to the AF or NP, and the AF may weaken and protrude from its normal anatomic space pushed by the internal NP as can be seen in FIG. 33. In more severe cases, the AF 3 may rupture and allow extravasation of the NP 4 contents to the surrounding anatomy (as depicted in FIG. 34). Symptoms may arise when the herniation (bulge) or leakage of the NP through the defect 9 in the AF 3 impinges on the nerve root 2 or spinal cord 1. There are many therapies currently utilized for treatment of the herniation (bulge) and resultant pain, starting with conservative therapies such as bed rest and pain medicines, to epidural injections, to open or minimally invasive discectomies or to complete discectomy and fusion of the disc space and adjacent vertebrae. An object of this invention is to provide a minimally invasive means to contain leakage or to reduce the bulge or defect 9 created by one of the invasive treatment means in an annulus to prevent impingement on the nerve roots or spinal canal.

Figure 35:
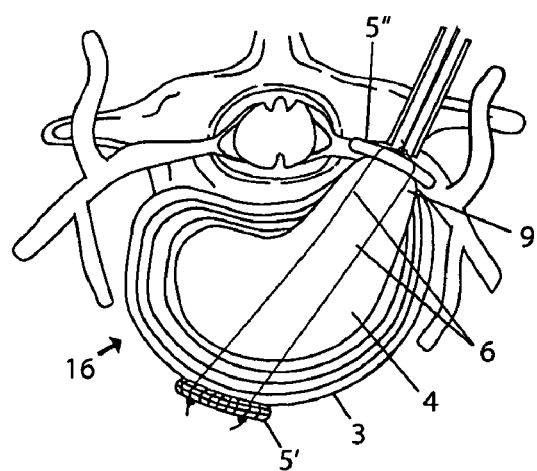
FIGS. 35-38 depicts the placement of various closure or treatment devices of the present invention.
Figure 36:
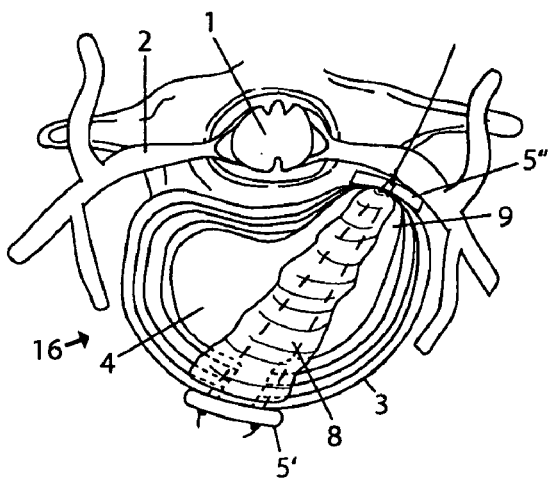

The previously described embodiments may also be useful for treating herniated or bulging annulus defects. FIG. 35 illustrates an additional embodiment of the device specifically envisioned for the treatment of bulging or herniated discs. The treatment device consists of a distal barrier 5' which is arranged to rest against the external aspect of the AF 3 directly opposite the bulge 9 in disc 16 in the anterior-lateral portion of the AF 3. Connecting elements 6 traversing through the AF 3 and NP 4, connects the distal barrier element 5' to another barrier, proximal barrier 5", which is arranged to rest against the bulge 9 in the affected part of the AF 3 in the posterior part of the disc. The barriers 5' & 5", as previously described may be constructed of a resorbable polymer, resorbable collagen or other resorbable or non-resorbable material. The barriers 5' and 5" may be somewhat flexible, but not so much as to pull through the delivery opening or defect 9 upon the application of compression. In the preferred embodiment, barrier 5' is comprised of a flexible membrane such as a polyethylene mesh and barrier 5" is a more rigid material such as an injection molded plastic. The barriers 5' and 5" may also contain small barbs or points 7 (as can be seen in FIG. 10A) to interface with the internal or external surface of the AF 3 to prevent dislodging. Connecting members 6 may preferably be a suture, similar to that described above, and may be manufactured from polymers known in the art, including synthetic and natural polymers. In some embodiments of the device, the connecting member may also be associated with a sealing element 8, as has been described above. The sealing or intermediate component 8 may be arranged within the walls of the annulus 4, as shown in FIG. 11, and/or all or a portion of the NP 4, as shown in FIG. 36. The intermediate component or sealing member 8 may function to prevent the escape of NP through the defects 9 or openings created by the implanting of the closure device. In an embodiment, the intermediate material or sealing member 8 may be treated with fibrin glue or other means by which it can stick to the opening or defect 9, or alternatively may serve to deliver at least one therapy, drug or biologically active agent, such as those listed in Table 2. It is recognized the suture or connecting member 6 itself may feature a coating of a sealing material or a therapy that may be delivered upon implantation in the living being. All of the closure device components, including barriers 5, sealing member 8 and connecting members 6 may be non-resorbable for permanent implantation, partially resorbable, or completely resorbable, such that a temporary implant may be achieved.

Figure 37:
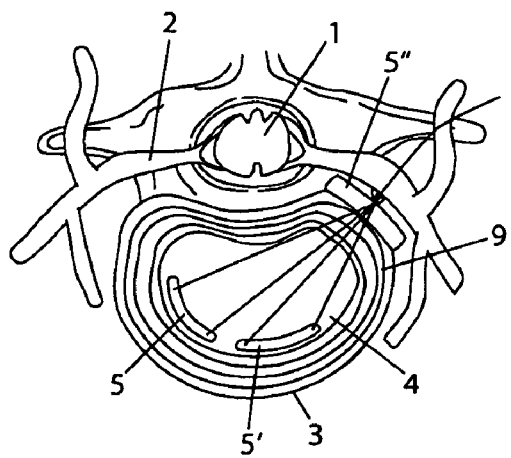

It is recognized that various other combinations of barrier placement are possible, varying in location and number. Barrier locations may vary within a given embodiment, such as is depicted in FIG. 37, having multiple distal barriers 5' against an interior aspect of the annulus 3 and within the nucleus 4, and having a proximal barrier 5" inside of the nucleus, inside the annulus, replacing a portion of the annulus, or exterior to the annulus. As shown here and in some other embodiments, the placement of multiple barriers may be necessary to provide the necessary levels of support. Such multiple barriers placements may be seen in the exemplary embodiment of FIG. 37 where multiple distal barriers 5' are operating in parallel to maintain tension upon connecting members 6 and upon proximal barrier 5".

Figure 38:
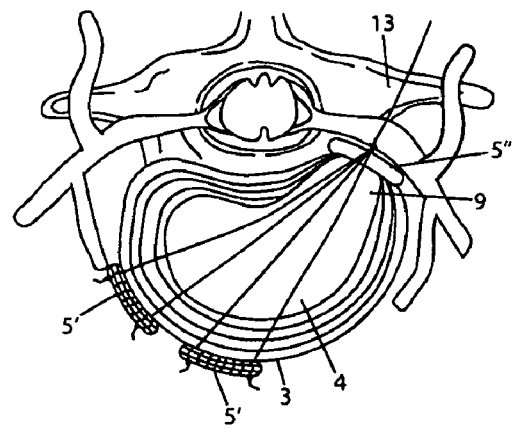

In an alternative embodiment of the device envisioned for the treatment of bulging or herniated discs, as depicted in FIG. 38, the device features multiple barrier members 5' which are arranged to rest against the exterior aspect of the AF 3 opposite the bulge 9 in disc 16 in the anterior-lateral portion of the AF. The placement of multiple barrier members as shown herein serve to provide increased surface area over which to distribute a given load, which will necessarily be less than the load per unit area imposed by a single similarly sized barrier placed against a bulge or defect 9, thereby overcoming the bulge and restoring the normal appearance of the annulus 3.

With reference to FIGS. 35 and 36, depicting the process for repair of a defect 9 in the form of a hernia (bulge). In practicing this embodiment of the present invention for the repair of a herniated disc or bulge or defect 9 in the annular wall 3, a cannula or access sheath 13 and obturator 14, as described above with reference to repairing a partial or full defect in the annular wall, may be inserted percutaneously and directed towards the annular wall, preferably towards the defect 9 in the annulus. As described previously, once the cannula 13 has passed through the soft tissue and is resting in the proper location against the annulus 3, ideally at the location of the herniation or bulge 9, the obturator 14 is removed and a trocar or tissue dilator 18 may be inserted and may be advanced into and/or through the annulus, thereby creating or expanding an aperture for the insertion of the delivery device. Furthermore, and in the case where the barrier 5' is to be rested against the outer aspect of the opposing portion of the AF 3, the trocar or tissue dilator 18 may be advanced through the opposite AF as well. The insertion of the trocar may be performed using standard techniques known in the art. Upon verification of placement of the trocar completely through the disc 16, such as is possible through the employment of monitoring features such as detection location features (e.g., calibration of the trocar, radiographic visualization, or other means) the delivery device 15 housing the closure device may be inserted through the access sheath 13, and through the nucleus 4 space, exiting the opposite side of the AF.

Once the delivery device has been passed through the AF, NP and opposite AF the deployment of the fastener device is performed to arrive at the embodiment as depicted in FIGS. 35 and 36 having a distal barrier 5' external to the annulus 3. The steps for deployment and securement of the fastener components may be achieved in a manner similar to that described previously with reference to FIGS. 19-32, altering the components and placements as needed to achieve the desired outcome.

Alternatively, the delivery device may remain within the NP and not extended out the opposite AF, and may deploy one or more distal barrier 5' against the internal aspect of the AF 3, with the result as depicted in FIG. 37. Deployment may occur by depositing the closure device components into place from the delivery sheath 15, for example, by utilizing a rod or other pushing device directed through the delivery sheath from a proximal location, which upon contacting one or more components of the closure device causes each component to exit the distal end of the delivery sheath. The location of each component of the device may be confirmed by various monitoring mechanisms as known in the art, e.g., radiopaque or other visible markers in combination with x-ray imaging or fluoroscopic imaging, positional markings or bands, etc.

Subsequently, and preferably as the delivery device 15 and/or access sheath 13 is retracted, the connecting member 6, such as a suture may be deployed, optionally in conjunction with a soft intermediate component or sealing member 8 of the device, as can be seen in FIG. 36. As previously described, the intermediate component 8 may be made of a polymer material, and may be resorbable (e.g., collagen). Furthermore, the intermediate component may contain some bioactive substance, therapy, or drug, such as those listed in Table 2. It is recognized that any of the resorbable or non-resorbable components utilized in the practice of the invention may also beneficially delivery a biologically active agent as well, such as pain reducing or inflammatory reducing agents, or other drugs. The intermediate component 8 including any bioactive substance, either together, or alone, may act to improve the healing of the defect. It is recognized the intermediate component 8 may be made of a rigid polymer similar to the barrier 5. Compression may be applied to the AF 3 and the bulge defect 9 upon removal of the delivery device 15 and/or annular sheath 13 from the disc 16, and deployment of holding mechanism or fastening element 17 (e.g., an automatic slip knot) which when pushed against the proximal barrier 5", or in the case of a rigid intermediary component, the holding element may be pushed against the intermediary component 8, and maintains tension upon the connecting member 6. This tension results in compression created between barriers 5' and 5", such that the act of compression alone may act to reduce the bulge defect 9 in the AF 3, thereby relieving or preventing impingement on the nerve root 2 or spinal cord 1, and resulting pain or harm. Additionally, the implanted fastener or closure device may act to prevent subsequent extravasation of the contents of the NP 4 through the bulge or defect 9, and may provide a scaffold, such as may occur if made of a collagen or other porous material, to support the regeneration of the AF. The internal connector or coupling mechanism 6, extending out from the disk proximally may then be removed at a convenient location to encourage healing, e.g., such as being severed at the surface of the skin, in order minimizing irritation, inflammatory response and opportunity for infection.

Repair of the Annulus Fibrosis Secondary to Placement of a Nucleus Pulposus Implant Material Newer approaches to the repair of the degenerated intervertebral disc and specifically the degenerated NP have envisioned the removal, replacement, and/or augmentation of the natural NP material with an artificial nucleus replacement material designed to mimic the natural mechanical properties of the NP. In this manner, normal disc function may be restored by the insertion of a synthetic or natural material through the annulus and into the nucleus.

Figure 39:
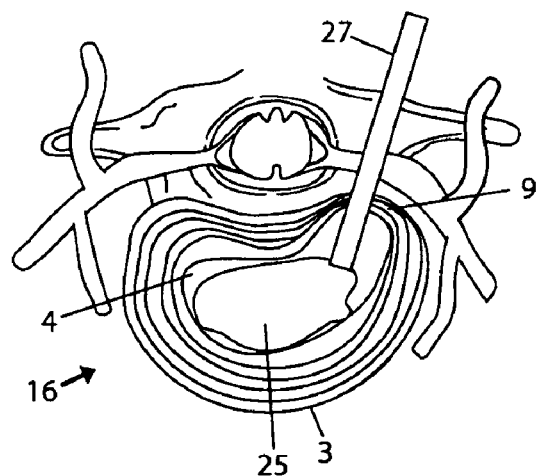
FIG. 39 illustrates overhead cross-sectional views of a vertebral disc having a nucleus implant material placed into the nucleus.

As can be seen in FIG. 39, the nucleus replacement implant material 25 may be a material capable of being delivered by a delivery apparatus 27 (for example, being injected via a needle, cannula or other suitable instrument, or being placed through a cannula, sheath or other suitable instrument), into the region of the nucleus 4, either with, or without removing the existing NP. The material 25 may then remain entrapped, either permanently or temporarily, within the annulus 4, and restore the natural mechanical function of the nucleus pulposus 4. Examples of materials suitable for injecting and serving as a nucleus replacement include synthetic or natural hydrogels (e.g., collagen gels, PEC gel, etc.) Alternatively, an injectable implant material 25 may be injected as a liquid, hydrogel, or paste, and harden or cure in-situ to become a self-supporting implant material 25. This material may serve to supplement the mechanical properties of the degenerated NP, or in the case of complete nucleus removal, the implant material would replace the NP and mimic the natural biomechanical and viscoelastic properties of the disc.

Alternatively, the nucleus implant material 25 may be a self-supporting material, resilient or otherwise (e.g. solids, porous foam, collapsible resilient cage, disc or stent structure, etc.), at the time of being implanted. There are currently several developmental attempts to address this approach, most notably in the form of a device utilizing a partially hydrolyzed polyacrylonitrile housed within a polyethylene jacket (manufactured by Raymedica), and an implant utilizing Aquacryl 90 which is a modified poly-acrylonitrile (PAN) that can take up to 90% of its weight in water (manufactured by Replication Medical). This material is bonded to internal Dacron meshes and is partially hydrated and upon insertion provides anisotropic axial expansion.

The self-supporting implant material 25 utilized in this embodiment of the present invention may be provided in various shapes or conformations (e.g., collapsed, preshaped to a particular portion of the disc or the entire disc, etc.). The implant material 25 may be implanted in a first conformation, and following implantation take on a second conformation, for example, a collapsible implant may expand after being placed within the nucleus due to physical means or rehydration, and arrive at a second conformation due to the anisotropic properties of the material.

In the practice of the technique of NP replacement or augmentation, the integrity of the natural AF 3 would necessarily be compromised to allow the insertion of the implant material. For example, in order to facilitate delivery of the NP filling implant material 25, and in the case of an injectable implant material 25, a delivery apparatus 27 in the form of a needle may be directed through the soft tissue to the outer level of the AF 3, then through the AF and into the nucleus 4 in order to deliver the implant material 25. The delivery apparatus 27 upon penetrating through the AF, may be directed through an existing defect, or alternatively may create a defect 9, which may or may not require repair through the techniques described herein. It is also a technique that a cannula/obturator may be a suitable delivery apparatus 27 for a nucleus replacement implant material 25, and may be inserted to the level of the AF 3, an opening created either through the placement of multiple trocars through the AF or alternatively through the use of a coring/cutting tool to create a lumen in the AF for the removal of the NP and subsequently for the injection of the material. Alternatively, for a solid implant material 25, an opening in the AF must be created to allow the removal of the degenerated NP and insertion of the implant material. In order to implant solid or self-supporting devices whose size is at or near that required to fill the nuclear space 4, a relatively large opening or defect 9 must be utilized or created in the AF 3 to allow removal of the NP material and insertion of the self-supporting implant material 25. If left un-repaired, there have been reports in the literature of expulsion of such devices. It is recognized that a collapsible or deformable self-supporting implant may serve to minimize the opening required to implant the device. In any event, it is desirable to contemplate the filling and repair of the defect 9 in the AF 3 to reduce the risk of expulsion of the implant material 25 and to support the repair and regeneration of the AF. Furthermore, in order to prevent potential extravasation of the filling material 25 after implantation, and to reinforce the mechanical integrity of the AF 3 or to potentially regenerate the AF, a fastener or closure device of the present invention may be utilized to ensure that the opening created in the AF to deliver the NP filling material is closed, as can be seen with reference to FIG. 11, where the nucleus 4 would be replaced with an implant material (not shown). The implant materials 25 contemplated may utilize natural matricies, which can facilitate or enhance the in-growth of cells and tissue and ultimately facilitate the regeneration of the AF, providing a more natural construct.

Following the implantation of the artificial NP implant material 25 (whether injectable or self-supporting), the fastener or closure device of the present invention may be directed through the same access opening in the annulus through which the injection or insertion occurred, to seal the opening or defect 9. This repair may occur in a substantially similar manner as has been described with reference to any of the techniques described above for repairing a defect in the annulus, particularly the techniques described to treat the defect remaining in a discectomy procedure. These techniques are particularly well suited for repairing defects that are created through the use of injectable nucleus replacement materials. Especially in the case of NP repair or replacement with a solid implant, there may be a need to repair a much larger breach in the AF.

Any or all of the embodiments of the present invention may beneficially incorporate a location detection means that is capable of providing for accurate positioning and placement of the device by sensing or otherwise allowing the detection of the location of the device within the anatomy. More specifically, the location detection means may allow the detection of the location of the device in order to ensure the proper placement of the components of the device within the annulus, nucleus, and/or the interface between the annulus and nucleus. Additionally, the location detection means may also serve as a locking member to maintain a position of at least a portion of the device with respect to the body.

Various methods disclosed herein could be used for such purposes. One embodiment would include the use of an expanding balloon or an articulating wing or finger to locate the interface between the nucleus and annulus, and assure proper placement of the closure or treatment device. By way of example, the delivery instrument could have an expandable or reconfigurable member (e.g. flange, balloon, anchor, finger, foot plate, etc.) that can be used to help locate the transition between the annulus and nucleus or other adjacent tissues. Such expandable or reconfigurable members could help provide an indication of proper location for device placement as well as help to create a physical space into which a device can be implanted. The system could be advanced into the appropriate tissue and then the expandable or reconfigurable element could be activated, the device could be withdrawn, advanced, or otherwise manipulated until an indicator provides a signal that the device is at the desirable location.

Concepts of this approach could employ "tactile feel" as one indicator, to sense when a delivery system is at the appropriate location. Similarly, sensors may be utilized at or near the distal end of the device to confirm placement, such as an optical sensor or pressure sensor that may be exposed to tissue during placement of the device, and enable confirmation of accurate placement of the device.

It is recognized that such an expandable or reconfigurable member may also beneficially serve to stabilize the disc, and or the components of the invention during and after placement of the device. Additionally, other stabilizing components may be utilized to achieve proper placement of the device, such as a sliding ring, flange, or other component that may be delivered following the insertion of a delivery tube or sheath, and placed against the target site, or the surrounding tissues to lend stability to the device. As can be seen with reference to FIGS. 36-46, and to be discussed in further detail below, the expandable member may be expanded against the annulus interior wall, thereby preventing the retraction of the positioning device from the nucleus, and stabilizing the positioning member. Optionally, a slidable flange may be advanced along the body of the positioning device in order to apply securing pressure against the exterior of the annulus, or other tissue, thereby maintaining the accurate placement of the positioning device. The flange may be advanced by external application of force, or alternatively, may be advanced by operation of an advancing mechanism, such that the slidable flange is directed towards the distal end of the positioning device.

In another embodiment of a location detection means, a cannula or access sheath may be provided having a separate pathway (e.g. a lumen) for providing a location probe. The separate pathway may have an exit port located at or near the distal end of the delivery system. A flexible or reconfigurable member may be extended, either through the device, or from the device, and allow the surgeon to gauge the nature of the tissue, such as through tactile feel. A member being inserted into nucleus pulposus material would relay tactile information that the tissue is soft, as it would easily yield to advancement of the probe. In contrast, the tough fibrous annulus material would provide greater resistance to the advancement of the probe, affording similar confirmation of placement of the device.

In another embodiment, the location detection means may rely on calibrated insertable components, such as needles, delivery sheaths, or cannulas, which may be provided having graduated markings to indicate depth of penetration, and allow proper placement of the repairing components of the device.

It is also recognized that the use of markers or bands (e.g. radiographic markers, visual markers, etc.) may provide location information for any of the described embodiments, such as through the use of radiographic techniques (e.g. MRI, X-ray, etc.), and further aid in ensuring the proper placement of the device of the present invention.

Thus since the invention disclosed herein may be embodied in other specific forms without departing from the spirit or general characteristics thereof, some of which forms have been indicated, the embodiments described herein are to be considered in all respects illustrative and not restrictive, by applying current or future knowledge. The scope of the invention is to be indicated by the appended claims, rather than by the foregoing description, and all changes which come within the meaning and range of equivalency of the claims are intended to be embraced therein.

TABLE 1

Examples Of Suitable Materials

Aliphatic polyesters
Bioglass
Cellulose
Chitin
Collagen
    Types 1 to 20
    Native fibrous
    Soluble
    Reconstituted fibrous
    Recombinant derived
Copolymers of glycolide
Copolymers of lactide
Elastin
Fibrin
Glycolide/l-lactide copolymers (PGA/PLLA)
Glycolide/trimethylene carbonate copolymers (PGA/TMC)
Hydrogel
Lactide/tetramethylglycolide copolymers
Lactide/trimethylene carbonate copolymers
Lactide/$\epsilon$-caprolactone copolymers
Lactide/$\sigma$-valerolactone copolymers
L-lactide/dl-lactide copolymers
Methyl methacrylate-N-vinyl pyrrolidone copolymers
Modified proteins
Nylon-2
PHBA/$\gamma$-hydroxyvalerate copolymers (PHBA/HVA)
PLA/polyethylene oxide copolymers
PLA-polyethylene oxide (PELA)
Poly (amino acids)
Poly (trimethylene carbonates)
Poly hydroxyalkanoate polymers (PHA)
Poly(alklyene oxalates)
Poly(butylene diglycolate)
Poly(hydroxy butyrate) (PHB)
Poly(n-vinyl pyrrolidone)
Poly(ortho esters)
Polyalkyl-2-cyanoacrylates
Polyanhydrides
Polycyanoacrylates
Polydepsipeptides
Polydihydropyrans
Poly-dl-lactide (PDLLA)
Polyesteramides
Polyesters of oxalic acid
Polyethylene Glycol
Polyethylene Oxide
Polyglycan Esters
Poly(Glycerol Sebacate)
Polyglycolide (PGA)
Polyiminocarbonates
Polylactides (PLA)
Poly-l-lactide (PLLA)
Polyorthoesters
Poly-p-dioxanone (PDO)
Polypeptides
Polyphosphazenes
Polysaccharides
Polyurethanes (PU)
Polyvinyl alcohol (PVA)
Poly-$\beta$-hydroxypropionate (PHPA)
Poly-$\beta$-hydroxybutyrate (PBA)
Poly-$\sigma$-valerolactone
Poly-$\beta$-alkanoic acids
Poly-$\beta$-malic acid (PMLA)
Poly-$\epsilon$-caprolactone (PCL)
Pseudo-Poly(Amino Acids)
Starch
Trimethylene carbonate (TMC)
Tyrosine based polymers
Alginate
Bone allograft or autograft
Bone Chips
Calcium
Calcium Phosphate
Calcium Sulfate
Ceramics
Chitosan TABLE 1-continued Examples Of Suitable Materials Cyanoacrylate
Collagen
Dacron
Demineralized bone
Elastin
Fibrin
Gelatin
Glass
Gold
Glycosaminoglycans
Hydrogels
Hydroxy apatite
Hydroxyethyl methacrylate
Hyaluronic Acid
Liposomes
Mesenchymal cells
Nitinol
Osteoblasts
Oxidized regenerated cellulose
Phosphate glasses
Polyethylene glycol
Polyester
Polysaccharides
Polyvinyl alcohol
Platelets, blood cells
Radiopacifiers
Salts
Silicone
Silk
Steel (e.g. Stainless Steel)
Synthetic polymers
Thrombin
Titanium
Tricalcium phosphate

TABLE 2

Examples of Biologically Active Agents

Adenovirus with or without genetic material
Alcohol
Amino Acids
   L-Arginine
Angiogenic agents
Angiotensin Converting Enzyme Inhibitors (ACE inhibitors)
Angiotensin II antagonists
Anti-angiogenic agents
Antiarrhythmics
   Amiodarone
   Lidocaine
   Sotalol
   Procainamide
   Diltiazem
Anti-bacterial agents
Antibiotics
   Erythromycin
   Penicillin
   Imipenem
   Zosyn
   Cipro
   Flagyl
   Vancomycin
Anti-coagulants
   Heparin
   Lovenox
Anti-Fungals
Anti-growth factors
Anti-inflammatory agents
   Dexamethasone
   Prednisone
   Aspirin
   Hydrocortisone
Antioxidants
Anti-platelet agents TABLE 2-continued Examples of Biologically Active Agents Forskolin
GP IIb-IIIa inhibitors
eptifibatide
Anti-proliferation agents
   Rho Kinase Inhibitors
   (+)-trans-4-(1-aminoethyl)-1-(4-pyridylcarbamoyl)
   cyclohexane
Anti-rejection agents
Anti-restenosis agents
   Adenosine $A_{2A}$ receptor agonists
   Rapamycin
Antisense
Anti-thrombogenic agents
   Argatroban
   Fondaparinux
   Hirudin
   GP IIb/IIIa inhibitors
Anti-TNF
Anti-viral drugs
Arteriogenesis agents
   acidic fibroblast growth factor (aFGF)
   angiogenin
   angiotropin
   basic fibroblast growth factor (bFGF)
   Bone morphogenic proteins (BMP)
   epidermal growth factor (EGF)
   fibrin
   granulocyte-macrophage colony stimulating factor
      (GM-CSF)
   hepatocyte growth factor (HGF)
   HIF-1
   Indian hedgehog (Inh)
   insulin growth factor-1 (IGF-1)
   interleukin-8 (IL-8)
   MAC-1
   nicotinamide
   platelet-derived endothelial cell growth factor (PD-ECGF)
   platelet-derived growth factor (PDGF)
   transforming growth factors alpha & beta
      (TGF-.alpha., TGF-beta.)
   tumor necrosis factor alpha (TNF-.alpha.)
   vascular endothelial growth factor (VEGF)
   vascular permeability factor (VPF)
Bacteria
Beta blocker
Blood clotting factor
Bone morphogenic proteins (BMP)
Calcium channel blockers
Carcinogens
Cells
   Stem cells
   Bone Marrow
   Blood cells
   Fat Cells
   Muscle Cells
   Umbilical cord cells
Chemotherapeutic agents
   5-FU
   Ceramide
   Cisplatin
   Cyclophosphamide
   Doxorubicin
   Flutamide
   Imatinib
   Levamisole
   Methotrexate
   Mitomycin
   Oxaliplatin
   Paclitaxel
   Tamoxifen
   Taxol
   Topotecan
   Vinblastine
Cholesterol reducers
Chondroitin
Clopidegrel (e.g., plavix)
Collagen Inhibitors TABLE 2-continued Examples of Biologically Active Agents Colony stimulating factors
Coumadin
Cytokines prostaglandins
Dentin
Etretinate
Genetic material
Glucosamine
Glycosaminoglycans
GP IIb/IIIa inhibitors
    L-703,081
Granulocyte-macrophage colony stimulating factor (GM-CSF)
Growth factor antagonists or inhibitors
Growth factors
    Autologous Growth Factors
    Bovine derived cytokines
    Cartilage Derived Growth Factor (CDGF)
    Endothelial Cell Growth Factor (ECGF)
    Epidermal growth factor (EGF)
    Fibroblast Growth Factors (FGF)
    Hepatocyte growth factor (HGF)
    Insulin-like Growth Factors (e.g. IGF-I)
    Nerve growth factor (NGF)
    Platelet Derived Growth Factor (PDGF)
    Recombinant NGF (rhNGF)
    Tissue necrosis factor (TNF)
    Tissue derived cytokines
    Transforming growth factors alpha (TGF-alpha)
    Transforming growth factors beta (TGF-beta)
    Vascular Endothelial Growth Factor (VEGF)
    Vascular permeability factor (VPF)
    Acidic fibroblast growth factor (aFGF)
    Basic fibroblast growth factor (bFGF)
    Epidermal growth factor (EGF)
    Hepatocyte growth factor (HGF)
    Insulin growth factor-1 (IGF-1)
    Platelet-derived endothelial cell growth factor (PD-ECGF)
    Tumor necrosis factor alpha (TNF-.alpha.)
Growth hormones
Heparin sulfate proteoglycan
HMC-CoA reductase inhibitors (statins)
Hormones
    Erythropoietin
Immoxidal
Immunosuppressant agents
Immune modulator agents
Inflammatory mediator
Insulin
Interleukins
Interlukins
    Interlukin-8 (IL-8)
Lipid lowering agents
Lipo-proteins
Low-molecular weight heparin
Lymphocites
Lysine
MAC-1
Methylation inhibitors
Morphogens
    Bone morphogenic proteins (BMPs)
Nitric oxide (NO)
Nucleotides
Peptides
Polyphenol
PR39
Proteins
Prostaglandins
Proteoglycans
    Perlecan
Radioactive materials
    Iodine - 125
    Iodine - 131
    Iridium - 192
    Palladium 103
Radio-pharmaceuticals
Secondary Messengers
    Ceramide
Signal Transduction Factors TABLE 2-continued Examples of Biologically Active Agents Signaling Proteins
Somatomedins
Statins
Stem Cells
Steroids
Sulfonyl
Thrombin
Thrombin inhibitor
Thrombolytics
Ticlid
Tumor necrosis factor
Tyrosine kinase Inhibitors
    ST638
    AG-17
Vasodilator
    Histamine
    Forskolin
    Nitroglycerin
Vitamins
    E
    C
Yeast
Ziyphi fructus

What is claimed is:

1. A treatment device for repairing a defect in the intervertebral disc of a living being, said device comprising;

an elongated instrument, at least one bridging member, a plurality of positioning elements, a plurality of passage means, and a plurality of connector members;

wherein when said elongated instrument is placed in or near the defect, (i) said elongated instrument delivers said at least one bridging member inside of the intervertebral disc at a first location;

(ii) said elongated instrument displaces said at least one bridging member from said first location to a second location at at least a portion of the defect;

(iii) said connector members deploy from said elongated instrument into tissue at or near the defect and engage said at least one bridging member such that said at least one bridging member is secured at said second location;

(iv) said positioning elements position a portion of said connector members to a location where the passage means intersects with said portion of said connector members; and (v) said plurality of passage means extend from a retracted condition to pierce the tissue surrounding the defect, become attached to said positioned portion of said connector members, and draw said portion of said connector members back through said pierced tissue as said plurality of passage means are retracted back to said retracted position;

wherein said at least one bridging member provides support to the intervertebral disc, and wherein the treatment comprises said support.

2. The device of claim 1, wherein said device additionally comprises a securement element, wherein said securement element is arranged to act cooperatively with said connector members to cause the securing of said at least one bridging member at said second location.

3. The device of claim 1, wherein said at least one bridging member is resorbable.

4. The device of claim 3, wherein said connector members are resorbable.

5. The device of claim 1, wherein said positioning elements are arranged to be deployed radially about a central axis of said elongated instrument.

6. The device of claim 5, wherein said positioning elements are three or more in number.

7. The treatment device of claim 1, wherein said positioning elements are arranged to temporarily extend axially from a portion of said elongated instrument.

8. The treatment device of claim 1, wherein said positioning elements are arranged to be retracted into said elongated instrument prior to removal of said device from a position in or near said defect.

\* \* \* \* \*